(12) United States Patent
Garg et al.

(10) Patent No.: US 12,372,542 B2
(45) Date of Patent: Jul. 29, 2025

(54) SYSTEMS AND METHODS FOR THE DETECTION OF PHENOLIC CANNABINOIDS

(71) Applicant: The Regents of the University of California, Oakland, CA (US)

(72) Inventors: Neil K. Garg, Los Angeles, CA (US); Evan R. Darzi, Tucson, AZ (US)

(73) Assignee: The Regents of the University of California, Oakland, CA (US)

( * ) Notice: Subject to any disclaimer, the term of this patent is extended or adjusted under 35 U.S.C. 154(b) by 728 days.

(21) Appl. No.: 17/755,309

(22) PCT Filed: Nov. 2, 2020

(86) PCT No.: PCT/US2020/058535
§ 371 (c)(1),
(2) Date: Apr. 26, 2022

(87) PCT Pub. No.: WO2021/087453
PCT Pub. Date: May 6, 2021

(65) Prior Publication Data
US 2022/0390475 A1     Dec. 8, 2022

Related U.S. Application Data

(60) Provisional application No. 62/928,981, filed on Oct. 31, 2019.

(51) Int. Cl.
*G01N 33/94*     (2006.01)
*G01N 21/33*     (2006.01)

(52) U.S. Cl.
CPC ........... *G01N 33/948* (2013.01); *G01N 21/33* (2013.01)

(58) Field of Classification Search
CPC .............................. G01N 21/33; G01N 33/948
(Continued)

(56) References Cited

U.S. PATENT DOCUMENTS 8,497,299 B2    7/2013    Mechoulam et al.
9,921,234 B1    3/2018    Lynn et al.
(Continued)

FOREIGN PATENT DOCUMENTS

EP           4051334 A1    9/2022
WO    2005067917 A1    7/2005
(Continued)

OTHER PUBLICATIONS

Lowe, E. R. et al, Analytical and Bioanalytical Chemistry 2005, 383, 523-531. (Year: 2005).*
(Continued)

*Primary Examiner* — Arlen Soderquist
(74) *Attorney, Agent, or Firm* — KPPB LLP

(57) ABSTRACT

Systems and methods for detecting $\Delta^9$-tetrahydrocannabinol ($\Delta^9$-THC) are described. In many embodiments, the detection of $\Delta^9$-THC can be achieved by oxidizing $\Delta^9$-THC to corresponding oxidized products. The oxidation of $\Delta^9$-THC can be achieved chemically or electrochemically. The oxidized products of $\Delta^9$-THC can exhibit different photophysical and electrochemical properties compared to $\Delta^9$-THC. Many embodiments implement integrating $\Delta^9$-THC detection into a multimodal marijuana breathalyzer device.

20 Claims, 23 Drawing Sheets

(58) Field of Classification Search
USPC .......................................................... 436/149
See application file for complete search history.

(56) References Cited

U.S. PATENT DOCUMENTS

| | | | | |
|---|---|---|---|---|
| 2009/0294298 | A1* | 12/2009 | Compton | G01N 27/49 |
| | | | | 205/780.5 |
| 2010/0184082 | A1 | 7/2010 | Wang | |
| 2018/0128843 | A1 | 5/2018 | Lucas et al. | |
| 2019/0209095 | A1 | 7/2019 | Kamath et al. | |
| 2020/0397340 | A1* | 12/2020 | Dweik | G01N 27/416 |
| 2020/0400695 | A1* | 12/2020 | Dweik | A61B 5/4277 |

FOREIGN PATENT DOCUMENTS

| | | |
|---|---|---|
| WO | 2006134386 A1 | 12/2006 |
| WO | 2017147687 A2 | 9/2017 |
| WO | 2018112458 A1 | 6/2018 |
| WO | 2018200794 A1 | 11/2018 |
| WO | 2021087453 A1 | 5/2021 |

OTHER PUBLICATIONS

Nissim, R. et al, Chemistry Central Journal 2015, 9, article 41, 7 pages. (Year: 2015).*
Wanklyn, C. et al, Chemistry Central Journal 2016, 10, article 1, 11 pages. (Year: 2016).*
Extended European Search Report for European Application No. 20882717.0, Search completed Oct. 13, 2023, Mailed Oct. 20, 2023, 11 pgs.
International Preliminary Report on Patentability for International Application PCT/US2020/058535, Report issued May 3, 2022, Mailed May 12, 2022, 5 pgs.
International Search Report and Written Opinion for International Application No. PCT/US2020/058535, Search completed Dec. 16, 2020, Mailed Jan. 27, 2021, 11 pgs.
"ElectraSyn 2.0 Package", Printed from "https://www.ika.com/en/Products-Lab-Eq/Electrochemistry-Kit-csp-516/" on Jul. 31, 2022, 20 pgs.
Ashton, "Adverse effects of cannabis and cannabinoids", British Journal of Anaesthesia, vol. 83, No. 4, Oct. 1999, pp. 637-649, doi: 10.1093/bja/83.4.637.
Balbino et al., "Electrochemical Study of Delta-9-Tetrahydrocannabinol by Cyclic Voltammetry Using Screen Printed Electrode, Improvements in Forensic Analysis", Sensors & Transducers, vol. 207, No. 12, Dec. 12, 2016, pp. 73-78, XP055698349, Retrieved from the Internet: URL:https://www.researchgate.net/profile/Marco_Balbino/publication/312086399_Electrochemical_Study_of_Delta-9-Tetrahydrocannabinol_by_Cyclic_Voltammetry_Using_Screen_Printed_Electrode_Improvements_in_Forensic_Analysis/links/586e918d08ae329d6214c37d.pdf.
Balbino et al., "The Application of Voltammetric Analysis of Delta 9-THC for the Reduction of False Positive Results in the Analysis of Suspected Marijuana Plant Matter", Journal of Forensic Sciences, vol. 61, No. 4, Feb. 29, 2016, pp. 1067-1073, XP055717615, Chicago, IL, US, ISSN: 0022-1198, DOI: 10.1111/1556-4029.13059.
Balbino et al., "Use of Screen-Printed Electrodes for Quantification of Cocaine and [Delta]9-THC: Adaptions to Portable Systems for Forensic Purposes", Journal of Solid State Electrochemistry, vol. 20, Springer, Berlin, DE, Sep. 2016, First published Feb. 19, 2016, pp. 2435-2443, XP036042221, ISSN: 1432-8488, DOI: 10.1007/S10008-016-3145-3 [retrieved on Feb. 19, 2016].
Balbino et al., "Voltammetric Determination of Delta9-THC in Glassy Carbon Electrode: An Important Contribution to Forensic Electroanalysis", Forensic Science International, vol. 221, No. 1, Mar. 20, 2012, pp. 29-32, XP028451730, ISSN: 0379-0738, DOI: 10.1016/J.FORSCIINT.2012.03.020 [retrieved on Mar. 23, 2012].
Compton, "Marijuana-Impaired Driving—A Report to Congress", NHTSA, Jul. 2017, 44 pgs.

Costanzo et al., "Portable FAIMS: Applications and future perspectives", International Journal of Mass Spectrometry, vol. 422, Nov. 2017, pp. 188-196, doi: 10.1016/j.ijms.2016.12.007.
Enache et al., "Phenol and para-substituted phenols electrochemical oxidation pathways", Journal of Electroanalytical Chemistry, vol. 655, No. 1, May 15, 2011, pp. 9-16, doi: 10.1016/j.jelechem.2011.02.022.
Hanus et al., "Phytocannabinoids: a unified critical inventory", Natural Products Report, vol. 33, No. 12, Nov. 23, 2016, pp. 1357-1392, doi: 10.1039/c6np00074f.
Hartman et al., "Cannabis Effect on Driving Skills", Clinical Chemistry, vol. 59, No. 3, Mar. 2013, Published online Feb. 2013, pp. 478-492, doi: 10.1373/clinchem.2012.194381.
Hartman et al., "Cannabis Effects on Driving Lateral Control With and Without Alcohol", Drug Alcohol Depend, vol. 154, Sep. 1, 2015, pp. 25-37.
Hazekamp et al., "Chromatographic and spectroscopic data of cannabinoids from *Cannabis sativa* L", Journal of Liquid Chromatography & Related Technologies, vol. 28, 2005, pp. 2361-2382, DOI: 10.1080/10826070500187558.
Himes et al., "Cannabinoids in exhaled breath following controlled administration of smoked cannabis", Clinical Chemistry, vol. 59, No. 12, Dec. 2013, Published online Sep. 17, 2013, pp. 1780-1789, doi: 10.1373/clinchem.2013.207407.
Hodjat-Kashani et al., Hashish: Oxidation of D8-Tetrahydrocannabinol (THC); Synthesis of D8-THC-1,2-Dione and 2-Hydroxy-D8-THC, Heterocycles, vol. 24, 1986, pp. 1973-1976, DOI:10.3987/R-1986-07-1973.
Hwang et al., "Tetrahydrocannabinol detection using semiconductor-enriched single-walled carbon nanotube chemiresistors", ACS Sensors, vol. 4, No. 8, 2019, Published online Aug. 1, 2018, pp. 2084-2093, doi: 10.1021/acssensors.9b00762.
Khan et al., "Synthesis and electrochemical properties of substituted para-benzoquinone derivatives", Tetrahedron Letters, vol. 51, No. 18, May 5, 2010, pp. 2541-2544, doi: 10.1016/j.tetlet.2010.03.007.
Kogan et al., "A Cannabinoid Quinone Inhibits Angiogenesis by Targeting Vascular Endothelial Cells", Molecular Pharmacology, vol. 70, No. 1, Jul. 2006, pp. 51-59, doi: 10.1124/mol.105.021089.
Kogan et al., "Synthesis and Antitumor Activity of Quinonoid Derivatives of Cannabinoids", Journal of Medicinal Chemistry, vol. 47, No. 15, Jan. 1, 2004, pp. 3800-3806, XP008048256, ISSN: 0022-2623, DOI: 10.1021/JM040042O.
Lenne et al., "The effects of cannabis and alcohol on simulated arterial driving: Influences of driving experience and task demand", Accident Analysis and Prevention, vol. 42, No. 3, May 2010, Available online Apr. 7, 2010, pp. 859-866, doi: 10.1016/j.aap.2009.04.021.
Lynch et al., "Correlation of breath and blood Δ9-tetrahydrocannabinol concentrations and release kinetics following controlled administration of smoked cannabis", Clinical Chemistry, vol. 65, No. 9, Sep. 2019, Published online Jul. 11, 2019, pp. 1171-1179, doi: 10.1373/clinchem.2019.304501.
Manolis et al., "The detection of delta 9-tetrahydrocannabinol in the breath of human subjects", Clinical Biochemistry, vol. 16, No. 4, Aug. 1, 1983, pp. 229-233, DOI: 10.1016/s0009-9120(83)90070-x.
Morales et al., "Synthetic cannabinoid quinones: Preparation, in vitro antiproliferative effects and in vivo prostate antitumor activity", European Journal of Medicinal Chemistry, vol. 70, Dec. 2013, pp. 111-119, doi: 10.1016/j.ejmech.2013.09.043.
Osman et al., "Bioactive Products from Singlet Oxygen Photooxygenation of Cannabinoids", European Journal of Medicinal Chemistry, vol. 143, Jan. 1, 2018, pp. 983-996, ISSN: Amsterdam, NL, ISSN: 0223-5234, DOI: 10.1016/j.ejmech.2017.11.043.
Quideau et al., "Iodane-mediates and electrochemical oxidative transformation of 2-methoxy- and 2-methylphenols", ARKIVOC, vol. 6, May 6, 2003, pp. 106-119.
Stang et al., "Organic Polyvalent Iodine Compounds", Chemical Reviews, vol. 96, No. 3, 1996, pp. 1123-1178, doi: 10.1021/cr940424.

(56) References Cited

OTHER PUBLICATIONS

Zimmer et al., "Oxidations with potassium nitrosodisulfonate (Fremy's radical). Teuber reaction", Chemical Reviews, vol. 71, No. 2, 1971, pp. 229-246.

* cited by examiner

SYSTEMS AND METHODS FOR THE DETECTION OF PHENOLIC CANNABINOIDS

CROSS-REFERENCED APPLICATIONS

This application is a national stage of PCT Patent Application No. PCT/US20/58535, entitled "Systems and Methods for the Detection of Phenolic Cannabinoids" to Garg et al., filed Nov. 2, 2020, which application claims priority to U.S. Provisional Application 62/928,981, entitled "Systems and Methods for the Detection of Tetrahydrocannabinol" to Garg et al., filed on Oct. 31, 2019, the disclosures of which are included herein by reference in their entireties.

STATEMENT OF FEDERAL FUNDING

This invention was made with government support under GM122245 awarded by the National Institutes of Health. The government has certain rights in the invention.

FIELD OF THE INVENTION

The present invention generally relates to apparatus and methods for tetrahydrocannabinol detection; and more particularly to optical and electrochemical methods to detect tetrahydrocannabinol oxidation product

BACKGROUND OF THE INVENTION

Marijuana has been used as a recreational drug for many millennia, with some reports of marijuana usage dating back to 3000 B.C. Its historic usage has been attributed to heightened sensations of euphoria, in addition to increased relaxation, amongst other effects. In modern times, marijuana has become one of the most commonly used drugs in the United States and many other countries. According to the 2018 Substance Abuse and Mental Health Service Administration (SAMHSA) national survey on drug use and health, approximately 45% of the general American population over the age of 12 years old (~124 million individuals) reported using marijuana in their lifetime. Of these reports, roughly 10% (>28 million individuals) reported using marijuana in the month prior to completing the survey.

Marijuana and other cannabinoid products have been considered illicit substances in many countries. However, over the past decade, there have been notable efforts to legalize these drugs for recreational purposes, which have led to the legalized use of marijuana. With the relaxation of laws and enforcement concerning marijuana, there has been a growing interest in safety, especially when it comes to driving motorized vehicles, akin to long-standing concerns about driving under the influence of alcohol. As of 2018, within the general population above sixteen years old, 4.6% (nearly 12 million individuals) reported driving under the influence of marijuana in the year prior to being surveyed. This can be striking given the well-known negative impact marijuana has on spatial and temporal judgment.

BRIEF SUMMARY

Systems and methods in accordance with various embodiments of the invention enable phenolic cannabinoids detection. In many embodiments, phenolic cannabinoids can be transformed to their corresponding quinones for detection. Examples of phenolic cannabinoids include (but are not limited to) tetrahydrocannabinol (THC or $\Delta^9$-THC), $\Delta^8$-THC, cannabinol (CBN), and cannabdiol (CBD). Several embodiments provide a method to detect phenolic cannabinol oxidation product. Many embodiments provide a method to detect tetrahydrocannabinol oxidation product. In many embodiments, oxidation of THC can be a controlled oxidation process. In several embodiments, the controlled oxidation process can generate tetrahydrocannabinol p-quinone (THCQ or $\Delta^9$-THCQ) from THC. In some embodiments, the oxidation process can be a chemical process. In certain embodiments, the oxidation process can be an electrochemical process. Many embodiments implement THC including (but not limited to) in gas phase and/or solution phase for detection. A number of embodiments detect property changes including (but not limited to) optical properties, electronic properties, and/or spectroscopic properties in oxidized THC products.

One embodiment of the invention includes a method of detecting tetrahydrocannabinol ($\Delta^9$-THC) comprising: obtaining a sample from a source; disposing the sample in a solution; oxidizing the sample either chemically or electrochemically; analyzing properties of the oxidized sample selected from the group consisting of photochemical properties, electronic properties, and spectroscopic properties; identifying tetrahydrocannabinol p-quinone ($\Delta^9$-THCQ) specific features in properties selected from the group consisting of photochemical properties, electronic properties, and spectroscopic properties; and determining if $\Delta^9$-THCQ is present in the oxidized sample.

In a further embodiment, the sample is either in liquid phase or in gas phase.

In another embodiment, the sample is a biological sample extracted from an individual and the biological sample is biofluid, tear, saliva, mucus, urine, sweat, blood, or plasma.

In a still further embodiment, the sample is in gas phase and the sample is breath.

In still another embodiment, the solution comprises an electrolyte dissolved in a solvent, wherein the solvent is selected from the group consisting of an aqueous solvent, an organic solvent, and a mixture of an aqueous solvent and an organic solvent.

In yet another embodiment, the solution comprises $NBu_4BF_4$, or $LiClO_4$ dissolved in a solvent, wherein the solvent is selected from the group consisting of an aqueous solvent, an organic solvent, and a mixture of an aqueous solvent and an organic solvent.

In a yet further embodiment, the solution comprises $NBu_4BF_4$ and a redox mediator N-hydroxytetrachlorophthalimide ($Cl_4NHPI$) and the sample is oxidized electrochemically.

In a yet further embodiment again, the solution comprises bis(trifluoroacetoxy)iodobenzene (PIFA) and the sample is oxidized chemically.

In another embodiment, the oxidizing process is a controlled electrochemical process.

In a further embodiment, $\Delta^9$-THCQ specific features in photochemical properties comprise optical absorbance in UV spectrum and visible light spectrum.

In yet another embodiment, optical absorbance of $\Delta^9$-THCQ in UV spectrum at wavelength between 200 nm and 300 nm, and in visible light spectrum at wavelength between 350 nm and 500 nm with a peak at around 402 nm.

In another additional embodiment, $\Delta^9$-THCQ specific features in electrochemical properties comprise at least one oxidation potential and at least one reduction potential.

In a yet further embodiment, the controlled oxidation of $\Delta^9$-THC to $\Delta^9$-THCQ has an efficiency of at least 20%.

In yet another embodiment, the controlled oxidation of $\Delta^9$-THC to $\Delta^9$-THCQ has an efficiency of at least 67%.

In a still further embodiment, the electrochemical oxidation comprises at least one cathode and at least one anode.

In another embodiment, the cathode is graphite, glassy carbon, or platinum.

In still another embodiment, the anode is graphite or platinum.

In still another embodiment, the cathode is graphite and the anode is platinum.

In a yet further embodiment, the cathode is platinum and the anode is platinum.

In yet another embodiment, the cathode is glassy carbon and the anode is platinum.

Still another additional embodiment includes a method of electrochemically oxidizing tetrahydrocannabinol ($\Delta^9$-THC) to $\Delta^9$-THC p-quinone ($\Delta^9$-THCQ) comprising: disposing a $\Delta^9$-THC sample in a solution; placing at least one cathode and at least one anode in electrical connection with the solution and applying a current there between; oxidizing the $\Delta^9$-THC sample; analyzing properties of the oxidized sample selected from the group consisting of photochemical properties, electronic properties, and spectroscopic properties; and identifying $\Delta^9$-THCQ specific features in properties selected from the group consisting of photochemical properties, electronic properties, and spectroscopic properties.

In a further embodiment, the sample is either in liquid phase or in gas phase.

In an additional embodiment, the sample is a biological sample extracted from an individual and the biological sample is biofluid, tear, saliva, mucus, urine, sweat, blood, or plasma.

In a still further embodiment, the sample is in gas phase and the sample is breath.

In yet another embodiment, the solution comprises an electrolyte dissolved in a solvent, wherein the solvent is selected from the group consisting of an aqueous solvent, an organic solvent, and a mixture of an aqueous solvent and an organic solvent.

In another embodiment, the solution comprises NBu$_4$BF$_4$ or LiClO$_4$ dissolved in a solvent, wherein the solvent is selected from the group consisting of an aqueous solvent, an organic solvent, and a mixture of an aqueous solvent and an organic solvent.

In still yet another embodiment, the solution comprises NBu$_4$BF$_4$ and a redox mediator N-hydroxytetrachlorophthalimide (CL$_4$NHPI).

In a further embodiment again, the oxidizing process is a controlled process.

In still another embodiment, $\Delta^9$-THCQ specific features in photochemical properties comprise optical absorbance in UV spectrum and visible light spectrum.

In a further additional embodiment, optical absorbance of $\Delta^9$-THCQ in UV spectrum at wavelength between 200 nm and 300 nm, and in visible light spectrum at wavelength between 350 nm and 500 nm with a peak at around 402 nm.

In a still further embodiment, $\Delta^9$-THCQ specific features in electrochemical properties comprise at least one oxidation potential and at least one reduction potential.

In yet another embodiment, the controlled oxidation of $\Delta^9$-THC to $\Delta^9$-THCQ has an efficiency of at least 20%.

In a further additional embodiment, the controlled oxidation of $\Delta^9$-THC to $\Delta^9$-THCQ has an efficiency of at least 67%.

In a still further embodiment, the cathode is graphite, glassy carbon, or platinum.

In a yet further embodiment, the anode is graphite or platinum.

In a yet another embodiment, the cathode is graphite and the anode is platinum.

In a further additional embodiment, the cathode is platinum and the anode is platinum.

In a still further embodiment, the cathode is glassy carbon and the anode is platinum.

Another further embodiment again includes an analyzer configured to detect the presence of $\Delta^9$-THC comprising a method as described.

Additional embodiments and features are set forth in part in the description that follows, and in part will become apparent to those skilled in the art upon examination of the specification or may be learned by the practice of the disclosure. A further understanding of the nature and advantages of the present disclosure may be realized by reference to the remaining portions of the specification and the drawings, which forms a part of this disclosure.

BRIEF DESCRIPTION OF THE DRAWINGS

The description will be more fully understood with reference to the following figures, which are presented as exemplary embodiments of the invention and should not be construed as a complete recitation of the scope of the invention, wherein.

DETAILED DESCRIPTION

Figure 1:
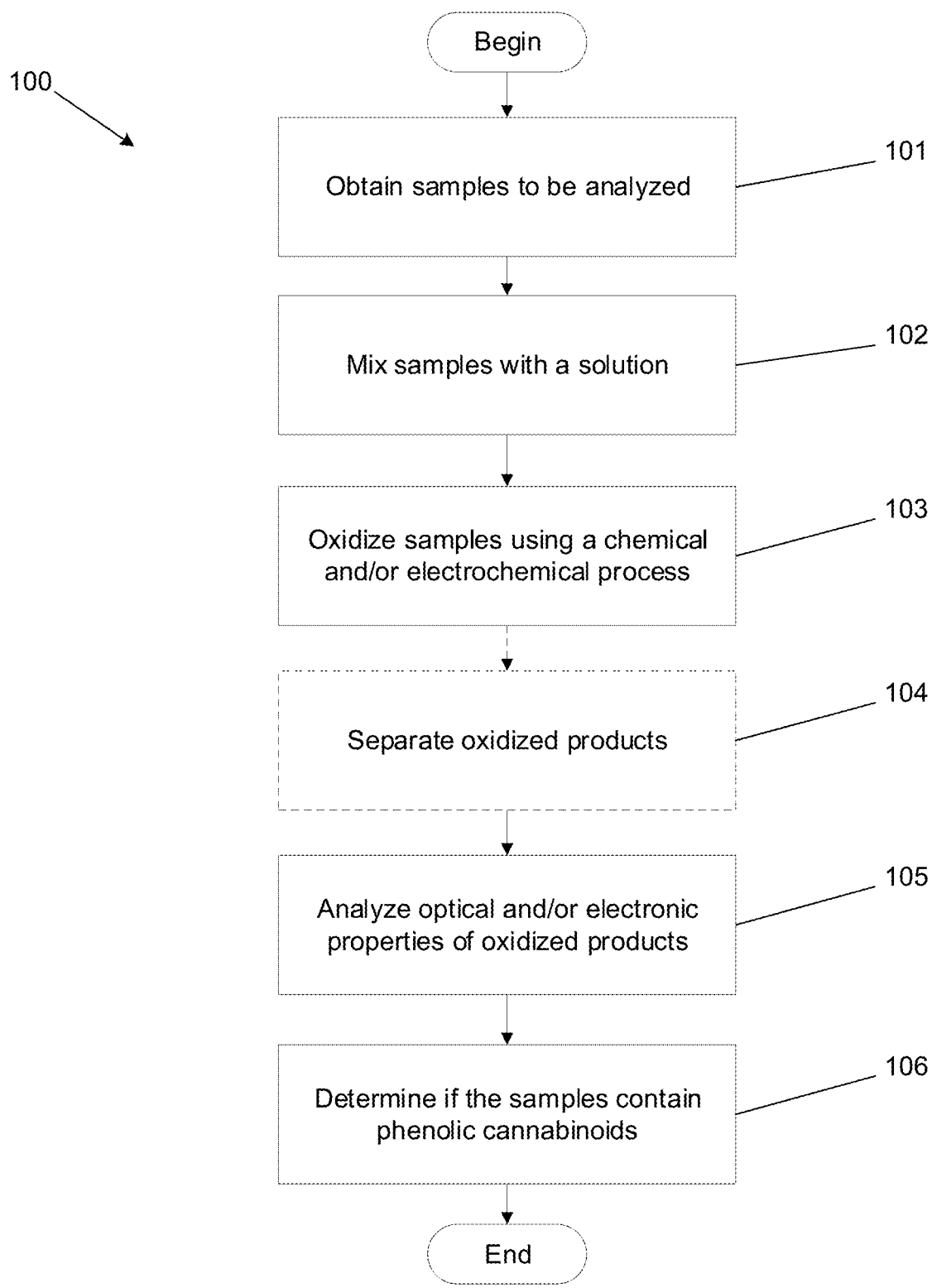
FIG. 1 illustrates a tetrahydrocannabinol detection process in accordance with an embodiment of the invention.

Turning now to the drawings, systems and methods for detecting phenolic cannabinol are described. Many embodiments implement an oxidation process to transform phenolic cannabinol to their corresponding quinones for detection. Examples of phenolic cannabinoids include (but are not limited to) tetrahydrocannabinol (THC or $\Delta^9$-THC), $\Delta^8$-THC, cannabinol (CBN), and cannabdiol (CBD). Several embodiments implement an oxidation process to transform THC to corresponding oxidized products for detection. Several embodiments implement a controlled oxidation process to transform THC to a corresponding tetrahydrocannabinol p-quinone (THCQ) for detection. In a number of embodiments, oxidized THC products including (but not limited to) THCQ can exhibit different properties than THC. Examples of different properties exihibited in oxidized THC products include (but are not limited to): photophysical properties, electronic properties, spectroscopic properties. In many embodiments, THCQ may show strong visible light absorbance and THC may not show visible light absorbance. In some embodiments, THCQ shows optical absorbance in the UV spectrum and visible spectrum. Several embodiments demonstrate that THCQ can exihibit strong absorbance peaks in the UV region at wavelength between 200 nm and 300 nm, and a strong peak in the visible light region. In many embodiments, THCQ can have different electrochemical properties including (but not limited to) redox potentials from THC. In several embodiments, THCQ can exhibit reduction potential electrochemically and THC may not possess reduction potential.

In some embodiments, THC oxidation can be a chemical process. In several embodiments, THC oxidation can be an electrochemical process. Many embodiments implement THC including (but not limited to) in gas phase and/or solution phase in the oxidation process for detection. In many embodiments, controlled oxidation of THC to THCQ can achieve at least 20% efficiency. Some embodiments implementing electrochemical oxidation process can achieve about 67% efficiency to oxidize THC to THCQ. Several embodiments implementing chemical oxidation process can achieve about 35% efficiency to oxidize THC to THCQ.

Many embodiments implement electrochemical processes to oxidize THC. In many embodiments, electrochemical oxidation processes use an electrochemical platform involving at least one cathode, at least one anode, at least on electrolyte, and at least one power source. Examples of cathode used in an electrochemical platform to oxidize THC include (but are not limited to): graphite, glassy carbon, platinum. Examples of anode used in an electrochemical platform to oxidize THC include (but are not limited to): graphite, platinum. As can readily be appreciated, any of a variety of cathode and/or anode material can be utilized as appropriate to the requirements of specific applications in accordance with various embodiments of the invention. Several embodiments implement a graphite cathode and a platinum anode in THC oxidation. Some embodiments implement a platinum cathode and a platinum anode in THC oxidation. Certain embodiments implement a glassy carbon cathode and a platinum anode in THC oxidation. Examples of electrolyte used in an electrochemical platform to oxidize THC include (but are not limited to): $NBu_4BF_4$, $LiClO_4$, $NBu_4PF_6$. As can readily be appreciated, any of a variety of electrolyte can be utilized as appropriate to the requirements of specific applications in accordance with various embodiments of the invention.

Systems and methods for oxidizing and detecting THC in accordance with various embodiments of the invention are discussed further below.

Phenolic Cannabinoids Detection Process

Many embodiments implement oxidation process including (but not limited to) chemical oxidation and/or electrochemical oxidation to oxidize phenolic cannabinoids including (but not limited to) tetrahydrocannabinol (THC or $\Delta^9$-THC), $\Delta^8$-THC, cannabinol (CBN), and cannabdiol (CBD) in solution phase and/or in gas phase to corresponding oxidized products for phenolic cannabinoids detection. A method for phenolic cannabinoids detection in accordance with an embodiment of the invention is illustrated in FIG. 1. The process 100 can begin by obtaining a sample to be analyzed (101). Some embodiments include solution samples including (but not limited to) biofluids, tear, saliva, mucus, urine, sweat, blood, plasma. In some embodiments, a sample is in gas phase. Gas phase samples can be obtained from (but not limited to) breath. In some embodiments, a biological sample extracted from an individual is used. In some embodiments, samples are put into solution or further diluted in a liquid. In some embodiments, samples are partially processed (e.g., centrifugation, filtration, etc.). In some embodiments, samples can be used as extracted from the source. As can readily be appreciated, any of a variety of solution samples can be utilized as appropriate to the requirements of specific applications in accordance with various embodiments of the invention.

Samples can be prepared by mixing with a solution (102). In many embodiments, the solution can be dissolved in a solvent including (but not limited to) aqueous solvent and/or organic solvent. In some embodiments, electrolyte can be used to mix with the samples. Examples of solution include (but are not limited to): $NBu_4BF_4$, $NBu_4BF_4$ in dry MeCN, $LiClO_4$, $NBu_4PF_6$. Several embodiment implement chemical oxidant including (but not limited to) bis(trifluoroacetoxy)iodobenzene (PIFA) to mix with samples. In some embodiments, redox mediator including (but not limited to) N-hydroxytetrachlorophthalimide ($Cl_4NHPI$), hydrogen peroxide ($H_2O_2$) can be added to solution. As can readily be appreciated, any of a variety of mixing solution can be utilized as appropriate to the requirements of specific applications.

In a number of embodiments, the mixed solutions can be loaded to a platform to be oxidized (103). Many embodiments implement a controlled oxidization process, where one corresponding oxidized product is generated. In a number of embodiments, phenolic cannabinoids can be oxidized to their corresponding quinones for detection. In certain embodiments, a controlled oxidization process includes oxidizing THC to THCQ. In several embodiments, the oxidization process is a chemical process. Chemical oxidization process in accordance with some embodiments can be carried out under ambient conditions such as at room temperature. In a number of embodiments, chemical oxidization process is a controlled process to oxidize THC to THCQ. In some embodiments, the oxidization process is an electrochemical process. In many embodiments, electrochemical oxidation processes use an electrochemical platform involving at least one cathode, at least one anode, and at least on electrolyte. Examples of cathode used in an electrochemical platform to oxidize THC include (but are not limited to): graphite, glassy carbon, platinum. Examples of anode used in an electrochemical platform to oxidize THC include (but are not limited to): graphite, platinum. As can readily be appreciated, any of a variety of cathode and/or anode material can be utilized as appropriate to the requirements of specific applications in accordance with various embodiments of the invention. Examples of electrolyte used in an electrochemical platform to oxidize THC include (but are not limited to): $NBu_4BF_4$. As can readily be appreciated, any of a variety of electrolyte can be utilized as appropriate to the requirements of specific applications in accordance with various embodiments of the invention. A current can be applied to the electrochemical platform to initiate oxidization process. Electrochemical oxidization process in accordance with some embodiments can be carried out under ambient conditions such as at room temperature. In certain embodiments, electrochemical oxidization process can be carried out between around 20° C. to around 25° C.

In several embodiments, oxidized samples can be separated and/or isolated (104). In various embodiments, the oxidized sample solution can be filtered and concentrated. In certain embodiments, the oxidized sample solution can be dried over a solid including (but not limited to) sodium sulfate, filtered, and concentrated. In many embodiments, separating oxidized samples can be an optional step. Oxidized samples can be analyzed directly after oxidization without being separated and/or isolated in accordance with certain embodiments.

In many embodiments, oxidized samples can be analyzed (105). Several embodiment implement analysis of the optical and/or electronic properties of the oxidized samples. Several embodiments can identify if oxidized products are present based on the signatures in optical spectra and/or electrochemical measurements. In a number of embodiments, oxidized phenolic cannabinoids products including (but not limited to) their corresponding quinones can exhibit different photophysical and/or electronic properties. Certain embodiments exihibit that oxidized THC products can have different photophysical properties and/or electronic properties than THC. While THC can have optical absorbance in the UV spectrum, oxidized THC products including (but not limited to) THCQ shows optical absorbance in both the UV spectrum and visible spectrum in accordance with some embodiments. Several embodiments demonstrate that THCQ can exihibit strong absorbance peaks in the UV region at wavelength between 200 nm and 300 nm, and a strong peak in the visible light region. In many embodiments, THCQ can have different electrochemical properties including (but not limited to) oxidation potentials and/or reduction potentials from THC.

Based on the analysis results, samples can be identified if they contain phenolic cannabinoids or not (106). As oxidized phenolic cannabinoids products have unique signatures, phenolic cannabinoids can be identified by the presence of its oxidized products. The optical spectral information and/or electrochemical measurements collected by the analysis step can be processed in real-time in accordance with several embodiments. In some embodiments, concentration of phenolic cannabinoids can be determined by how much oxidized products are present.

While various processes of detecting THC in a sample are described above with reference to FIG. 1, any of a process that includes various steps of the process can be performed in different orders and that certain steps may be optional according to some embodiments of the invention. As such, it should be clear that the various steps of the process could be used as appropriate to the requirements of specific applications. Furthermore, any of a variety of processes for detecting phenolic cannabinoids in a sample appropriate to the requirements of a given application can be utilized in accordance with various embodiments of the invention. Processes for detecting THC electrochemically in accordance with various embodiments of the invention are discussed further below.

Electrochemical Detection Process of
Tetrahydrocannabinol

Figure 2:
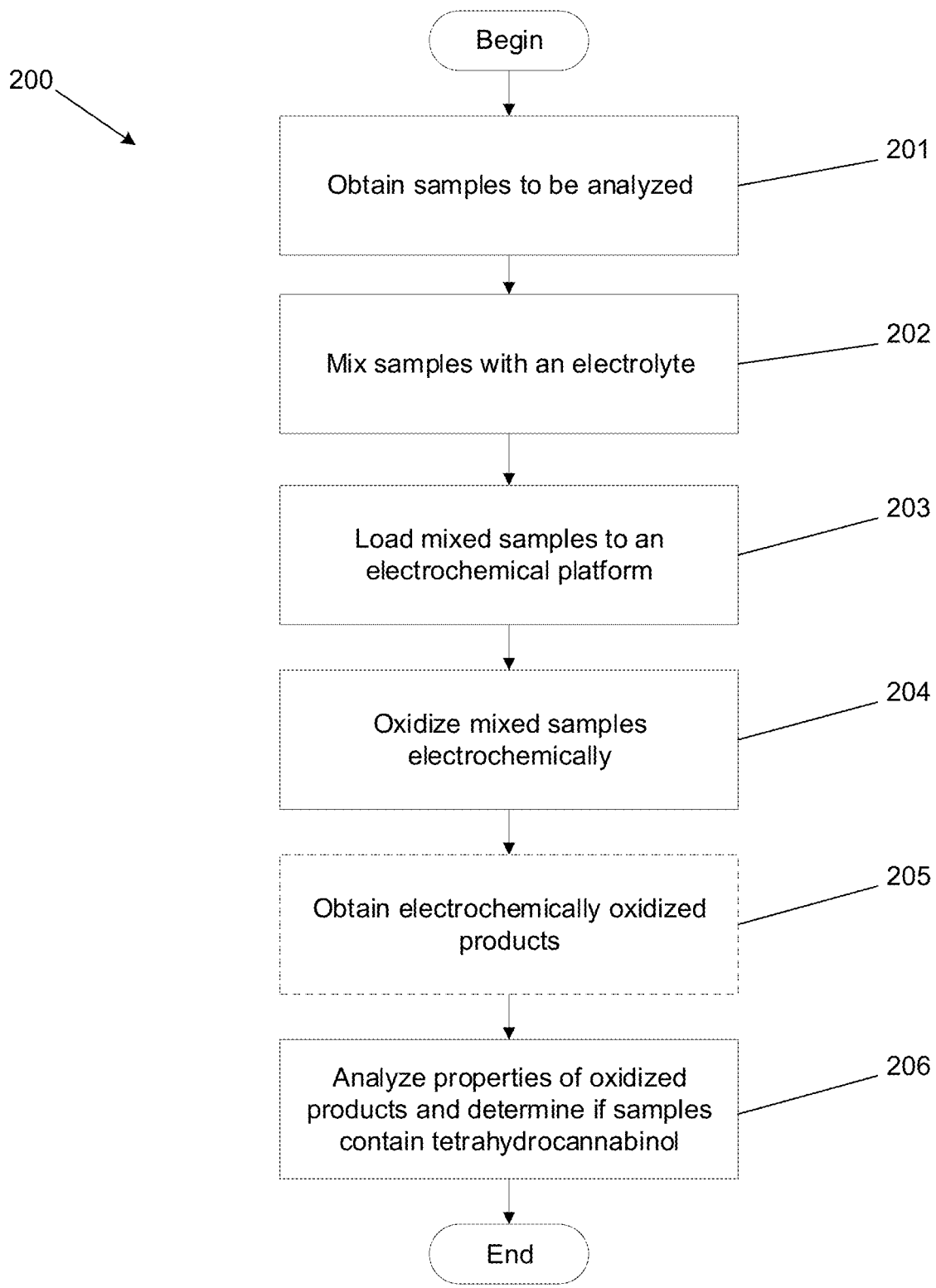
FIG. 2 illustrates a tetrahydrocannabinol electrochemical detection process in accordance with an embodiment.

Many embodiments implement electrochemical oxidation process to oxidize THC including (but not limited to) in solution phase and in gas phase to corresponding oxidized products for THC detection. A method for electrochemical detection of THC in accordance with an embodiment of the invention is illustrated in FIG. 2. The process 200 can begin by obtaining a sample to be analyzed (201). Some embodiments include solution samples including (but not limited to) biofluids, tear, saliva, mucus, urine, sweat, blood, plasma. In some embodiments, a sample is in gas phase. Gas phase samples can be obtained from (but not limited to) breath. In some embodiments, a biological sample extracted from an individual is used. In some embodiments, samples are put into solution or further diluted in a liquid. In some embodiments, samples are partially processed (e.g., centrifugation, filtration, etc.). In some embodiments, samples can be used as extracted from the source. As can readily be appreciated, any of a variety of solution samples can be utilized as appropriate to the requirements of specific applications in accordance with various embodiments of the invention.

Samples can be prepared by mixing with an electrolyte (202). In many embodiments, the electrolyte can be dissolved in a solvent including (but not limited to) aqueous solvent and/or organic solvent. Examples of electrolyte include (but are not limited to): $NBu_4BF_4$, $NBu_4BF_4$ in dry MeCN, $LiClO_4$. In some embodiments, redox mediator including (but not limited to) N-hydroxytetrachlorophthalimide ($Cl_4NHPI$), $H_2O_2$, tBuOOH, $NBu_4OH$, and $(tBuO)_2OPONBu_4$. As can readily be appreciated, any of a variety of electrolyte can be utilized as appropriate to the requirements of specific applications. In many embodiments, samples in gas phase can be directly applied to an electrolyte. Electrolyte can be in different environment including (but not limited to) in a container, on a substrate, and/or incorporated in a hydrogel in accordance with several embodiments.

In a number of embodiments, the mixed solutions can be loaded to an electrochemical platform (203) and oxidized electrochemically (204). Example of an electrochemical platform includes (but is not limited to): ElectraSyn™ plate by IKA. Many embodiments implement a controlled oxidization process, where one corresponding oxidized product is generated. In certain embodiments, a controlled oxidization process includes oxidizing THC to THCQ. In many embodiments, electrochemical oxidation processes use an electrochemical platform involving at least one cathode, at least one anode, and at least on electrolyte. Examples of cathode used in an electrochemical platform to oxidize THC include (but are not limited to): graphite, glassy carbon, platinum. Examples of anode used in an electrochemical platform to oxidize THC include (but are not limited to): graphite, platinum. As can readily be appreciated, any of a variety of cathode and/or anode material can be utilized as appropriate to the requirements of specific applications in accordance with various embodiments of the invention. A current can be applied to the electrochemical platform to initiate oxidization process. Electrochemical oxidization process in accordance with some embodiments can be carried out under ambient conditions such as at room temperature. In certain embodiments, electrochemical oxidization process can be carried out between around 20° C. to around 25° C. A number of embodiments investigate electrode combinations, applied current, electrolyte concentration, solvent to water ratio, and the effect of additives to determine the efficiency of oxidation process. Several embodiments implement a graphite cathode and a platinum anode in THC oxidation. Some embodiments implement a platinum cathode and a platinum anode in THC oxidation. Certain embodiments implement a glassy carbon cathode and a platinum anode in THC oxidation. In many embodiments, controlled oxidation of THC to THCQ can achieve at least 20% efficiency. Some embodiments implementing electrochemical oxidation process can achieve about 67% efficiency to oxidize THC to THCQ.

In several embodiments, electrochemically oxidized samples can be separated and/or isolated (205). In certain embodiments, the oxidized sample solution can be dried over a solid including (but not limited to) sodium sulfate, filtered, and concentrated. In many embodiments, separating oxidized samples can be an optional step. Oxidized samples can be analyzed directly after oxidization without being separated and/or isolated in accordance with certain embodiments.

In many embodiments, oxidized samples can be analyzed to identify if samples contain THC (206). Several embodiment implement analysis of the optical and/or electronic properties of the oxidized samples. Several embodiments can identify if oxidized products are present based on the signatures in optical spectra and/or electrochemical measurements. In a number of embodiments, oxidized THC products including (but not limited to) THCQ can exhibit different photophysical and/or electronic properties than THC. While THC can have optical absorbance in the UV spectrum, THCQ shows optical absorbance in both the UV spectrum and visible spectrum in accordance with some embodiments. Several embodiments demonstrate that THCQ can exihibit strong absorbance peaks in the UV region at wavelength between 200 nm and 300 nm, and a strong peak in the visible light region. In many embodiments, THCQ can have different electrochemical properties including (but not limited to) oxidation potentials and/or reduction potentials from THC. The optical spectral information and/or electrochemical measurements collected by the analysis step can be processed in real-time in accordance with several embodiments. In some embodiments, concentration of THC can be determined by how much oxidized products are present.

While various processes of detecting THC electrochemically in a sample are described above with reference to FIG. 2, any of a process that includes various steps of the process can be performed in different orders and that certain steps may be optional according to some embodiments of the invention. As such, it should be clear that the various steps of the process could be used as appropriate to the requirements of specific applications. Furthermore, any of a variety of processes for electrochemically detecting THC in a sample appropriate to the requirements of a given application can be utilized in accordance with various embodiments of the invention. Processes for detecting THC on a breathalyzer in accordance with various embodiments of the invention are discussed further below.

Tetrahydrocannabinol Detection with a Breathalyzer

Figure 3:
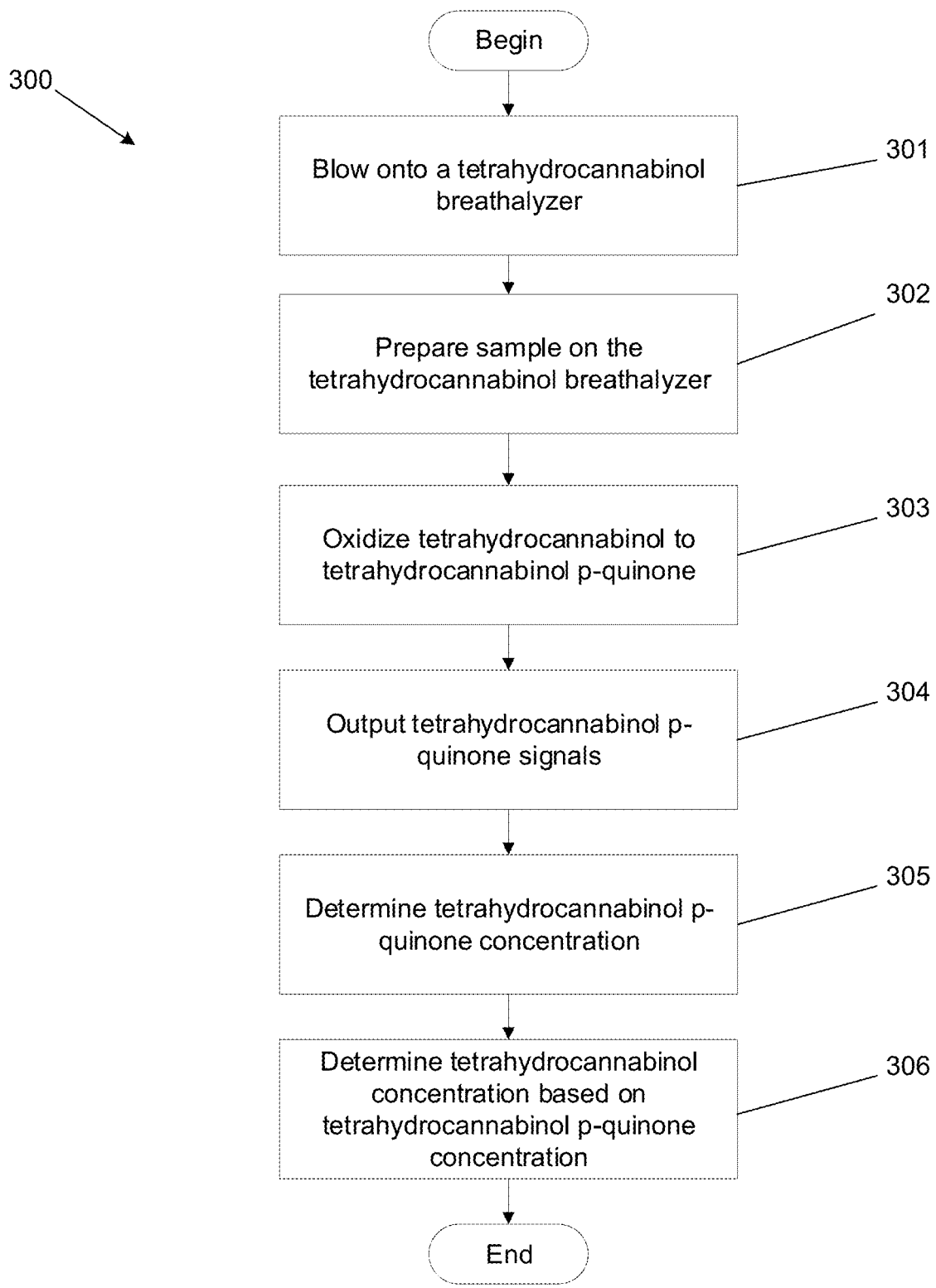
FIG. 3 illustrates a tetrahydrocannabinol detection process using a breathalyzer in accordance with an embodiment.

Many embodiments implement a device including (but not limited to) a breathalyzer that is able to oxidize THC in gas phase to corresponding oxidized products for detection. In many embodiments, THC detection can be carried out with a multimodal breathalyzer. A method for detecting THC with a breathalyzer in accordance with an embodiment of the invention is illustrated in FIG. 3. The process 300 can begin by obtaining a sample to be analyzed (301). In some embodiments, a sample is in gas phase. Gas phase samples can be obtained from (but not limited to) breath. In some embodiments, an individual can exhale into a collection device including (but not limited to) a breathalyzer for a certain time period. Within the sample collection device can be an analytic unit configured to electrochemically oxidize THC into THCQ. As can readily be appreciated, any of a variety to obtain gas phase samples for a breathalyzer can be utilized as appropriate to the requirements of specific applications in accordance with various embodiments of the invention.

Samples can be prepared by mixing with an electrolyte (302). In many embodiments, the electrolyte can be dissolved in a solvent including (but not limited to) aqueous solvent and/or organic solvent. Examples of electrolyte include (but are not limited to): $NBu_4BF_4$, $NBu_4BF_4$ in dry MeCN, $LiClO_4$. In some embodiments, redox mediator including (but not limited to) N-hydroxytetrachlorophthalimide ($Cl_4NHPI$), $H_2O_2$, tBuOOH, $NBu_4OH$, and $(tBuO)_2OPONBu_4$ can be added to solution. As can readily be appreciated, any of a variety of electrolyte can be utilized as appropriate to the requirements of specific applications. In many embodiments, samples in gas phase can be directly applied to an electrolyte. Electrolyte can be placed in various ways on the breathalyzer including (but not limited to) in a container, on a substrate, and/or incorporated in a hydrogel in accordance with several embodiments.

In a number of embodiments, the mixed solutions can be oxidized electrochemically on the breathalyzer (303). Many embodiments implement a controlled oxidization process, where one corresponding oxidized product is generated. In certain embodiments, a controlled oxidization process includes oxidizing THC to THCQ. In many embodiments, electrochemical breathalyzer includes at least one cathode, at least one anode, and at least one power source. Examples of cathode used in a breathalyzer to oxidize THC include (but are not limited to): graphite, glassy carbon, platinum. Examples of anode used in a breathalyzer to oxidize THC include (but are not limited to): graphite, platinum. As can readily be appreciated, any of a variety of cathode and/or anode material can be utilized as appropriate to the requirements of specific applications in accordance with various embodiments of the invention. A current can be applied to the breathalyzer to initiate oxidization process. Electrochemical oxidization process in the breathalyzer in accordance with some embodiments can be carried out under ambient conditions such as at room temperature. Certain embodiments operate the breathalyzer between around 20° C. to around 25° C.

In several embodiments, the breathalyzer can generate output signals for oxidized products (304). Oxidized samples can be analyzed directly after oxidization without being separated and/or isolated in accordance with certain embodiments. Several embodiment implement analysis of the optical and/or electronic properties of the oxidized samples. Several embodiments can identify if oxidized products are present based on the signatures in optical spectra and/or electrochemical measurements. In a number of embodiments, oxidized THC products including (but not limited to) THCQ can exhibit different photophysical and/or electronic properties than THC. The optical spectral information and/or electrochemical measurements collected by the analysis step can be processed in real-time in accordance with several embodiments.

In some embodiments, concentration of oxidized products including (but not limited to) THCQ can be determined based on the output signals (305). In several embodiments, concentration of THC can be determined by how much oxidized products are present (306).

While various processes of detecting THC in a sample with a breathalyzer are described above with reference to FIG. 3, any of a process that includes various steps of the process can be performed in different orders and that certain steps may be optional according to some embodiments of the invention. As such, it should be clear that the various steps of the process could be used as appropriate to the requirements of specific applications. Furthermore, any of a variety of processes for detecting THC with a breathalyzer appropriate to the requirements of a given application can be utilized in accordance with various embodiments of the invention.

Figure 4:
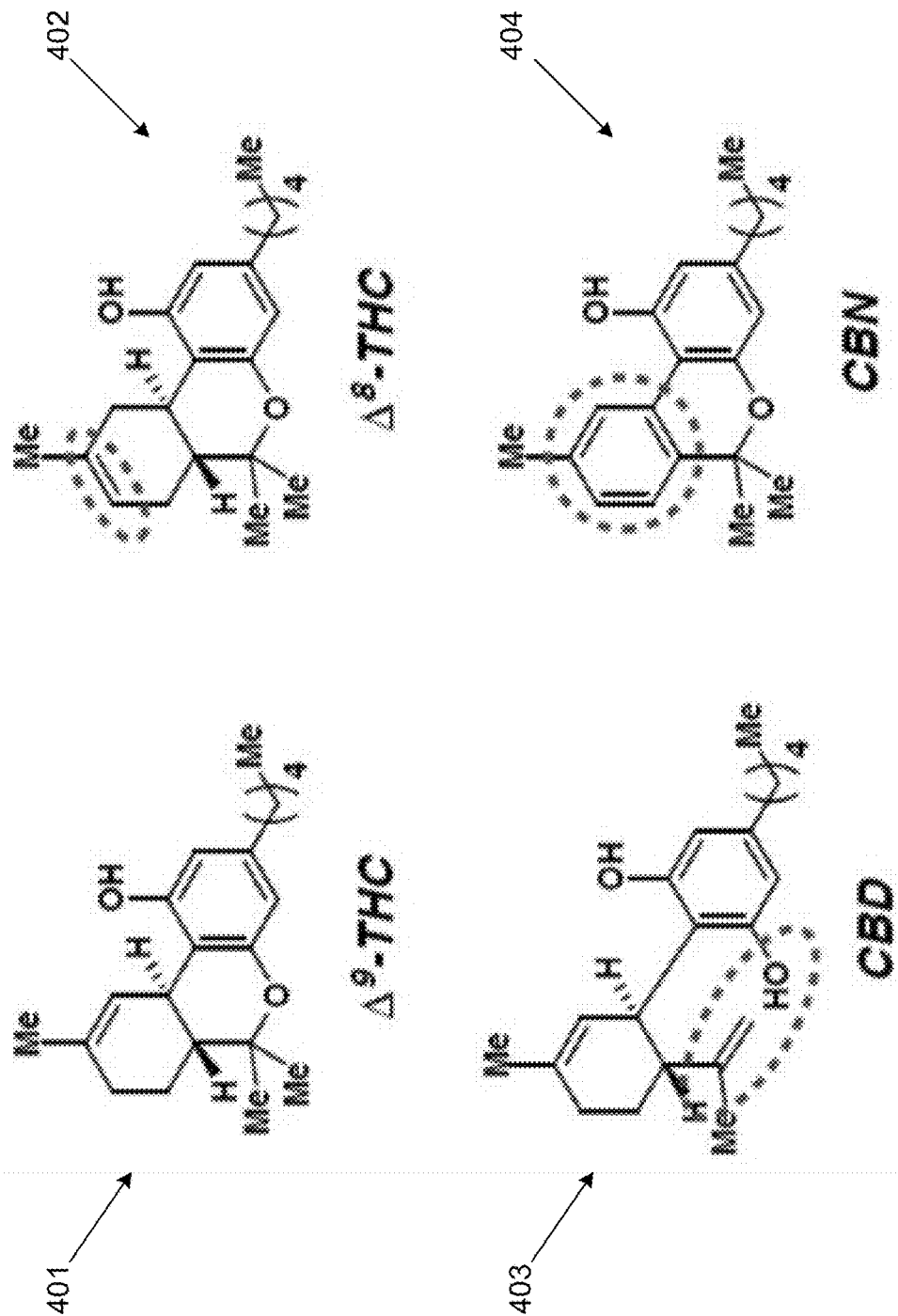
FIG. 4 illustrates the molecular structure of different phenolic cannabinoids in accordance with the prior art.

Tetrahydrocannabinol $\Delta^9$-tetrahydrocannabinol ($\Delta^9$-THC or THC) is one of at least 113 cannabinoids identified in cannabis. THC may be the principal psychoactive constituent of cannabis. With chemical name (—)-trans-$\Delta^9$-tetrahydrocannabinol, THC can refer to cannabinoid isomers. In many embodiments, THC and $\Delta^9$-THC are used exchangably to refer to tetrahydrocannabinol. In several embodiments, THCQ and $\Delta^9$-THCQ are used exchangably to refer to tetrahydrocannabinol p-quinone. FIG. 4 illustrates the chemical structure of different phenolic cannabinoids. 401 illustrates the chemical structure of $4^9$-THC. 402 illustrates the chemical structure of $\Delta^8$-THC. 403 illustrates the chemical structure of CBD. 404 illustrates the chemical structure of CBN.

Figure 5:
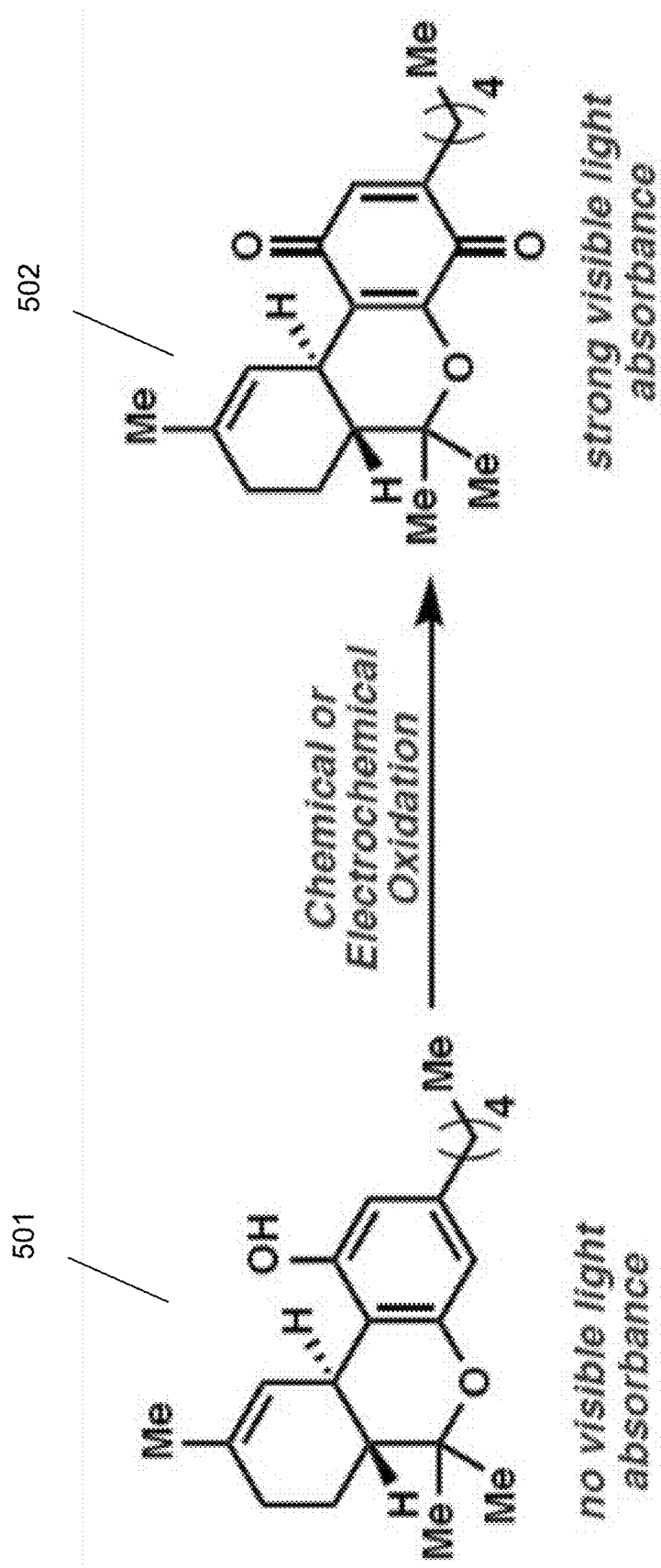
FIG. 5 illustrates the oxidation of $\Delta^9$-tetrahydrocannabinol ($\Delta^9$-THC) to corresponding p-quinone, $\Delta^9$-THCQ in accordance with an embodiment.

Many embodiments implement the detection of phenolic cannabinoids by transforming to their corresponding quinones. In some embodiments, the detection of $4^9$-THC by oxidizing $\Delta^9$-THC to corresponding p-quinone, $\Delta^9$-THCQ is demonstrated. An example of THC oxidizing to THCQ is illustrated in FIG. 5 in accordance with an embodiment of the invention. 501 illustrates THC in its chemical structure. 502 illustrates THCQ in its chemical structure. The oxidation of $\Delta^9$-THC in accordance to some embodiments can be achieved chemically and/or electrochemically. In several embodiments, the oxidized form of $\Delta^9$-THCQ can exihibit distinctly different photophysical and electrochemical properties compared to $\Delta^9$-THC. In many such embodiments, $\Delta^9$-THCQ shows strong visible light absorbance and $\Delta^9$-THC has no visible light absorbance. In other embodiments, $\Delta^9$-THCQ exhibits reduction potential electrochemically and $\Delta^9$-THC does not possess reduction potential. Many embodiments facilitate integrating $\Delta^9$-THC detection into a multimodal marijuana breathalyzer device.

Figure 6A:
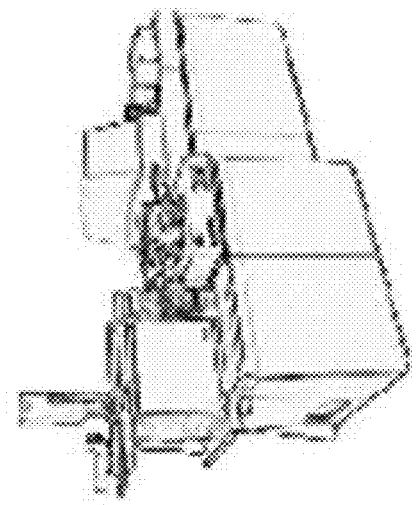
FIGS. 6A-6C illustrate $\Delta^9$-THC detection by mass spectrometry, covalent fluorescence tagging, and carbon nanotube chemiresistor in accordance to the prior art.
Figure 6B:
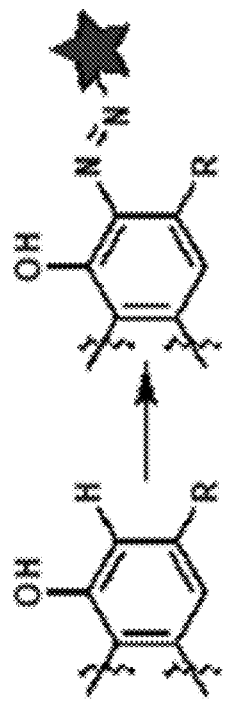
Figure 6C:
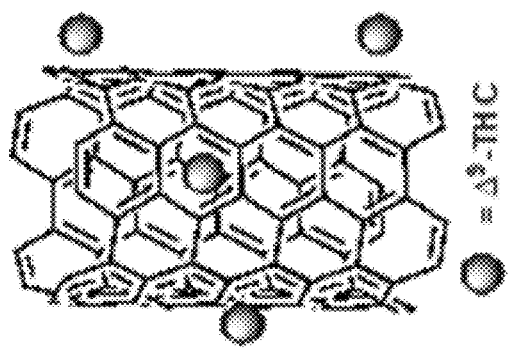

More than one hundred different cannabinoids can be present in marijuana, however, the primary psychoactive component responsible for driving impairment may be $\Delta^9$-THC. $\Delta^9$-THC can constitute between about 5-30 wt % of a marijuana source and can be a compound to identify when assessing potential marijuana usage. Current roadside tests for $\Delta^9$-THC impairment are time-consuming and may require special training, such as blood/saliva tests, or are based on behavioral signs and the officer's discretion. New chemical-based technologies can offer practical solutions for the growing problem of marijuana detection. Examples of THC detection methods are illustrated in FIGS. 6A-6C. FIG. 6A illustrates a $\Delta^9$-THC detection system including a specialized mass spectrometry. The mass spectrometry detection uses field asymmetric ion mobility spectrometry (FAIMS) requires specialized training, equipment, and can be time consuming. FIG. 6B illustrates a method using covalent modification for optical sensing. The covalent fluorescence tagging step may involve toxic reagents. FIG. 6C illustrates a chemiresistors based on carbon nanotube (CNT) adsorption method. Metallic CNT may vary in purity from batch to batch. Each method focuses on a single mode detection (mass spectrometry, photochemical, or electrochemical) to determine $\Delta$-THC levels. Correspondingly, each method may suffer from limitations including highly specialized equipment in the case of mass detection, toxic reagents used for covalent modification, and batch-to-batch variability in CNT sensing.

Figure 7:
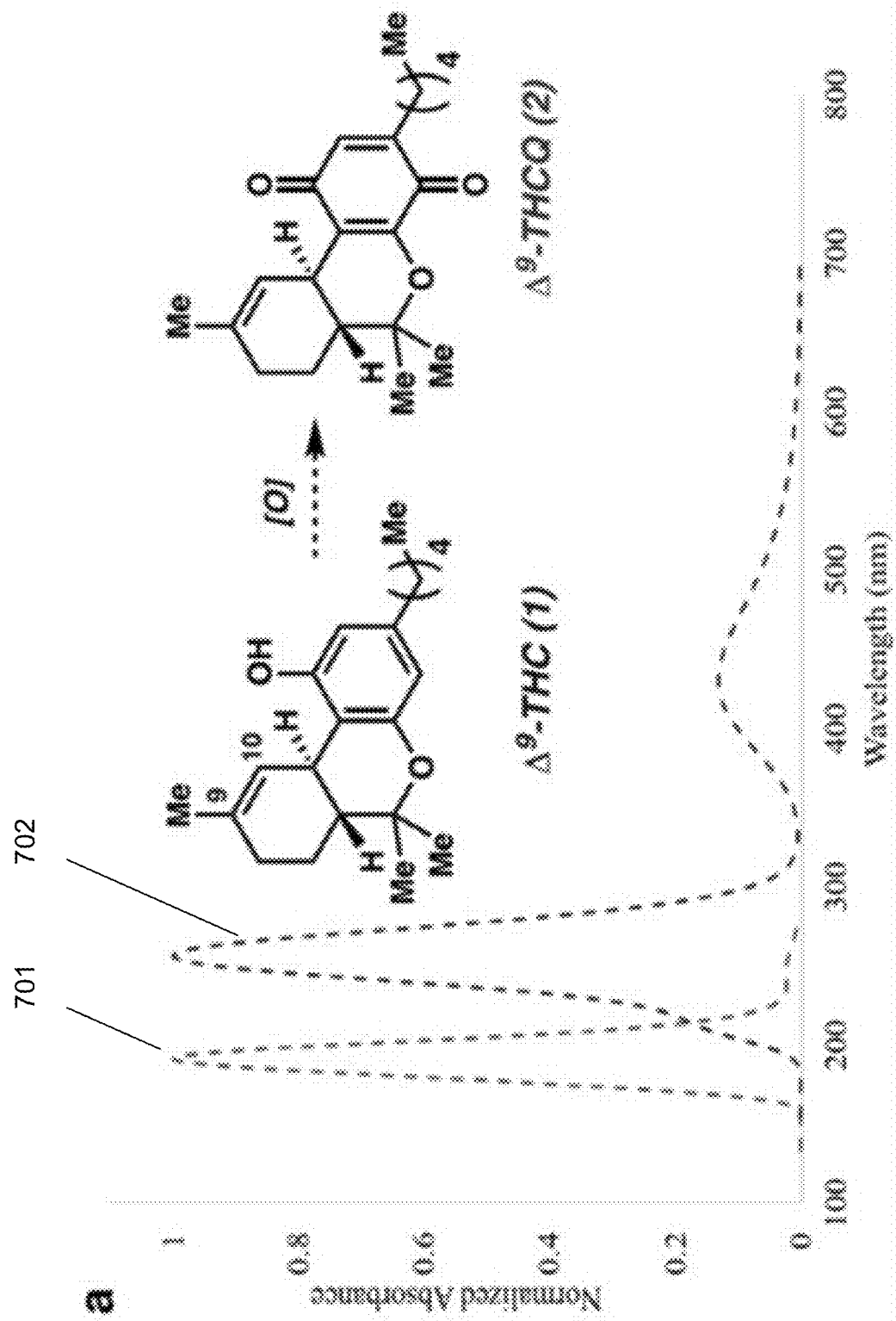
FIG. 7 illustrates a theoretical prediction of optical absorption of $\Delta^9$-THC and $\Delta^9$-THCQ in accordance with an embodiment.

Many embodiments implement transforming $\Delta^9$-THC to provide a derivative with diagnostic spectroscopic changes. An example of an oxidation process capable of transforming $\Delta^9$-THC into a corresponding p-quinone, $\Delta^9$-THCQ is illustrated in FIG. 7 in accordance with an embodiment of the invention. Time-dependent density functional theory (TDDFT) calculations show a shift in absorbance from the UV range for $\Delta^9$-THC (701) into the visible range for $\Delta^9$-THCQ (702). Oxidation in accordance with embodiments would result in a lowering of the LUMO to a range that can be measured electrochemically. The electrochemical transformation of $\Delta^9$-THC to $\Delta^9$-THCQ, in accordance to some embodiments, can provide a measurable change in both electrochemical and photochemical properties. The changes in electrochemical and photochemical properties, as well as a diagnostic change in mass, may be used independently and/or in combination with detection methods in accordance with several embodiments for the detection of $\Delta^9$-THC in samples. Processes for detecting THC using an electrochemical-based detection technology in accordance with various embodiments of the invention are discussed further below.

Electrochemical Oxidation of THC to THCQ

Chemical transformation of phenols to p-quinones has a rich history. The reaction typically may require stoichiometric reagents which generates toxic and/or undesirable side products (see, e.g., Zhdankin, V. V. & Stang, P. J., *Chem. Rev.* 1996, 96, 1123-1178., the disclosure of which is incorporated herein by reference), or utilizes shock sensitive reagents such as Fremy's salt (see, e.g., Zimmer, H., et al., *Chem. Rev.* 1971, 71, 229-246). Embodiments of the disclosure describe a process for performing a mild oxidation of $\Delta^9$-THC to its corresponding p-quinone isomer with a simple and robust electrochemical reaction without specialized reagents. In many embodiments, the $\Delta^9$-THC oxidation can be achievable both in solution and gas phase.

Figure 8A:
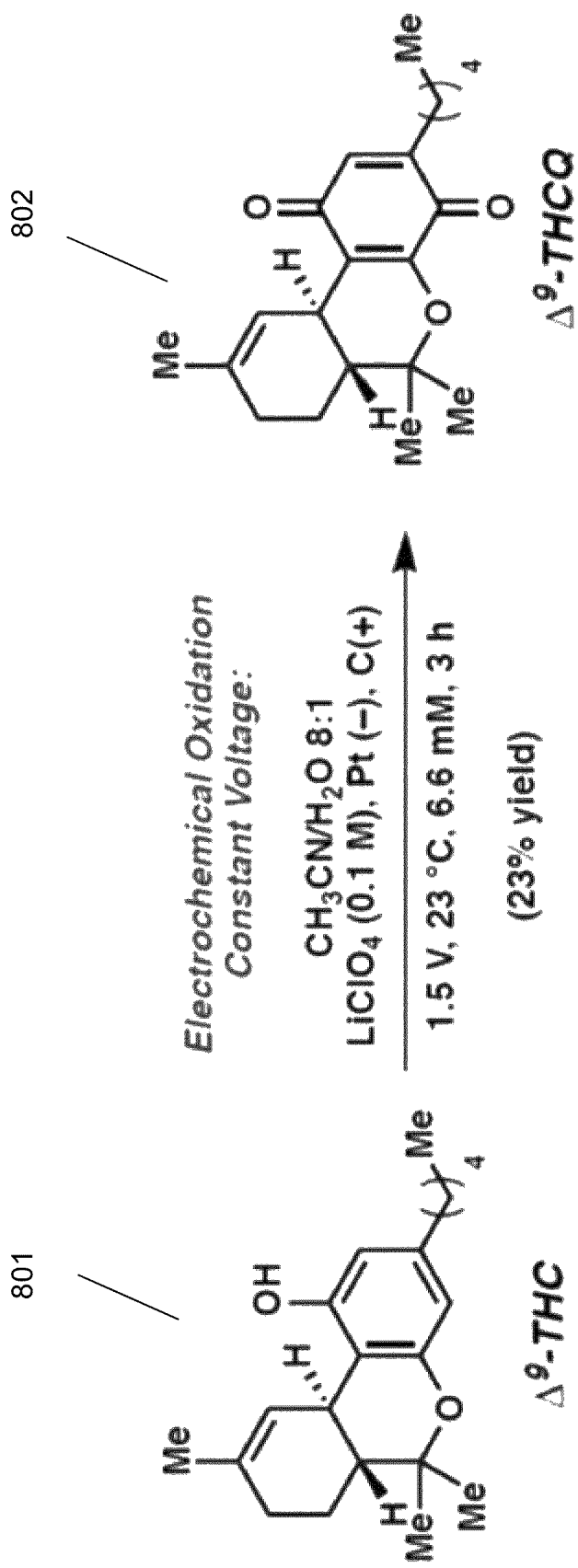
FIGS. 8A and 8B illustrate the electrochemical oxidation of $\Delta^9$-THC to $\Delta^9$-THCQ in accordance with an embodiment.
Figure 8B:
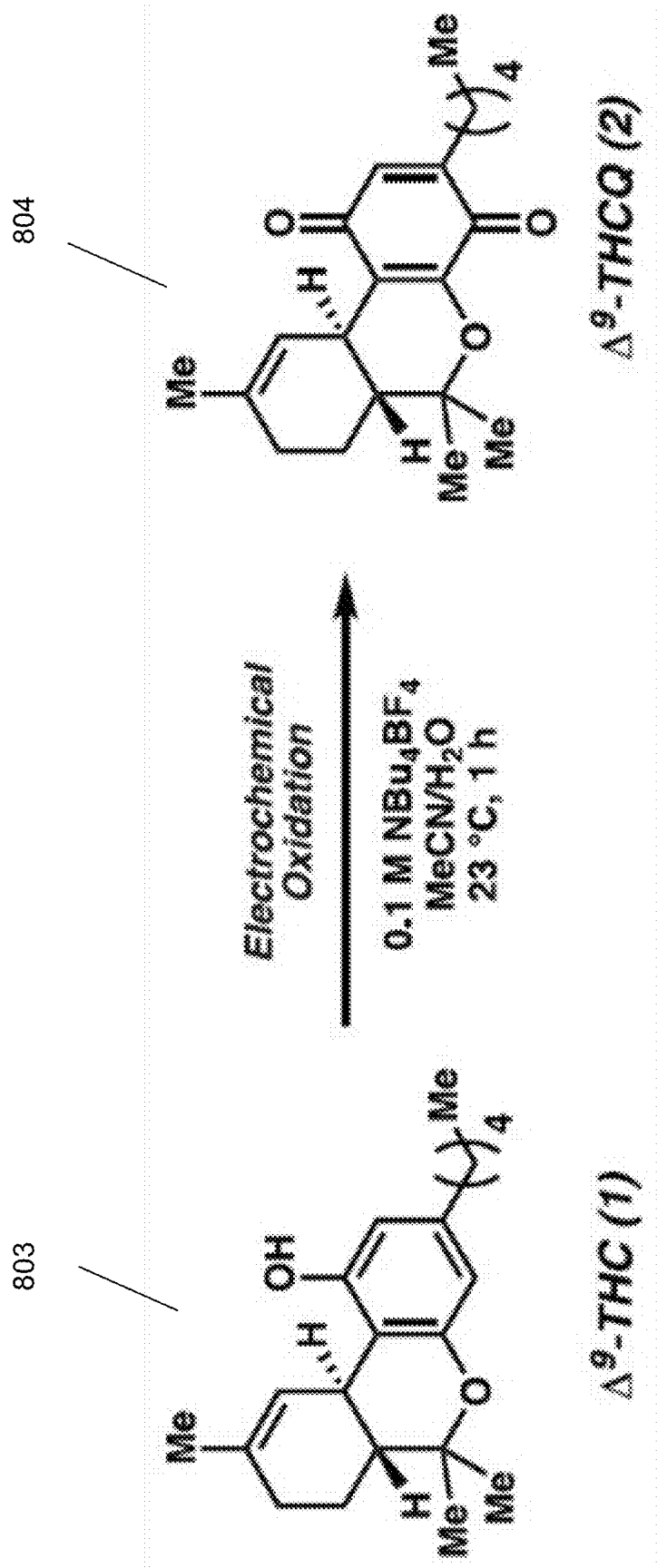

In many embodiments, the electrochemical oxidizing process can enable electrochemical phenolic oxidations to simple quinones and conversion of sterically congested dialkylphenols to their corresponding quinones. Examples of conditions and processes for the electrochemical oxidation of $\Delta^9$-THC to $\Delta^9$-THCQ in accordance to an embodiment are provided in FIGS. 8A-8B. FIG. 8A illustrates electrochemically oxidizing THC (801) to THCQ (802) in 0.1 M LiClO$_4$ electrolyte using a platinum (Pt) anode and a graphite cathode. During the reaction, a constant voltage of about 1.5 V is applied for about 3 hours at 23° C. to Δ$^9$-THC (23.3 µM) dissolved in 0.1 M LiClO$_4$ in CH$_3$CN. The reaction can achieve a full conversion of THC and about 23% yield of isolated THCQ. FIG. 8B illustrates electrochemically oxidizing THC (803) to THCQ (804) in 0.1 M NBu$_4$BF$_4$ electrolyte using a Pt anode and a graphite cathode. During the reaction, a constant current of about 7.9 mA is applied with alternating terminal polarity every 60 seconds for about 1 hour at 23° C. 0.1 M NBu$_4$BF$_4$ electrolyte is dissolved in CH3CN. The reaction can achieve a full conversion of THC and about 67% yield of isolated THCQ.

In various embodiments, electrochemical screening and reactions can be carried out using an ElectraSyn™ plate by IKA. The electrochemical reactions can be carried out in 0.1 M NBu$_4$BF$_4$ electrolyte dissolved in MeCN. During the reaction, a constant current of about 7.9 mA is applied with alternating terminal polarity every 60 seconds for about 1 hour at 23° C. This equipment evaluates a variety of reaction parameters (Table 1).

TABLE 1

Optimization of Reaction Conditions.

| Entry | Electrolyte (0.1 M) | Cathode/Anode | Current (mA) | % Yield |
|---|---|---|---|---|
| 1 | NBu$_4$BF$_4$ | C+/C− | 7.9 | 0 |
| 2 | NBu$_4$BF$_4$ | Pt+/Pt− | 7.9 | 30 |
| 3 | NBu$_4$BF$_4$ | Glassy C+/Pt− | 7.9 | 27 |
| 4 | NBu$_4$BF$_4$ | C+/Pt− | 7.9 | 67 |
| 5 | NBu$_4$BF$_4$ | C+/Pt− | 7.9 | 32* |

General conditions unless otherwise stated: Substrate (1) (1.00 equiv, 22.3 M), 6.60 mM (0.100 M NBu$_4$BF$_4$ in MeCN) MeCN:H$_2$O 8:1, 23° C., 1 h.
*Addition of 1 equiv of Cl$_4$NHPI.

In Entry 1 of Table 1, no conversion occurs when graphite is used as both the anode and cathode. However, changing the cathode and anode to platinum (Entry 2) can lead to full conversion of phenol (THC) and about 30% isolated yield of p-quinone (THCQ). Some embodiments implement a glassy carbon cathode and a Pt anode (Entry 3) and can achieve an isolated yield of about 27%. The use of graphite (Entry 4) in place of glassy carbon or platinum as an inexpensive alternative may achieve an isolated yield to about 67%. Accordingly, the electrochemical oxidation processes of embodiments are capable of forming the Δ$^9$-THCQ in high yield. Several embodiments using a redox mediator such as N-hydroxytetrachlorophthalimide (Cl$_4$NHPI) show an isolated yield of about 32% (Entry 5).

Electrochemical oxidation reactions in accordance with many embodiments may be performed in different conditions. Several embodiments assess a number of parameters including current, voltage, concentration, solvent to water ratio, and the effect of additives (Tables 2-6). It will be understood that these parameters may be used to optimize the electrochemical reactions according to embodiments to obtain specifically desired yields. Table 2 lists various cathode and anode combination in affecting THCQ yield. All entries in Table 2 are carried out in 0.1 M NBu$_4$BF$_4$ electrolyte dissolved in MeCN. During the reaction, a constant current of about 7.9 mA is applied for about 1 hour at 23° C. Entry 1 uses graphite as both cathode and anode and results in 0% oxidation to THCQ from THC. Entry 2 uses Pt as both cathode and anode, and achieves about 30% isolation yield of THCQ. Entry 3 uses classy carbon as cathode and Pt as anode, and achieves about 27% isolation yield of THCQ. Entry 4 uses graphite as cathode and Pt as anode, and is able to achieve about 67% isolation yield of THCQ from oxidizing THC.

TABLE 2

Effect of electrodes on % yield.

| Entry | Cathode/Anode | % Yield |
|---|---|---|
| 1 | C+/C− | 0 |
| 2 | Pt+/Pt− | 30 |
| 3 | Glassy C+/Pt− | 27 |
| 4 | C+/Pt− | 67 |

Table 3 lists various electrolyte concentration in affecting THCQ yield. All entries in Table 3 are carried out in 0.1 M NBu$_4$BF$_4$ electrolyte dissolved in MeCN with a Pt anode and a graphite cathode. During the reaction, a constant current of about 7.9 mA is applied with alternating terminal polarity every 60 seconds for about 1 hour at 23° C. In Entry 1, electrolyte (0.100 M NBu$_4$BF$_4$ in MeCN, 3.9 mM) is used followed by water (0.400 mL) and achieves about 10% isolation yield of THCQ from THC. In Entry 2, electrolyte (0.100 M NBu$_4$BF$_4$ in MeCN, 6.6 mM) is used followed by water (0.400 mL) and achieves about 67% isolation yield of THCQ from THC. In Entry 3, electrolyte (0.100 M NBu$_4$BF$_4$ in MeCN, 13 mM) is used followed by water (0.400 mL) and achieves about 17% isolation yield of THCQ from THC.

TABLE 3

Effect of concentration on % yield.

| Entry | Concentration | % Yield (brsm) |
|---|---|---|
| 1 | 3.9 mM | 10 (20) |
| 2 | 6.6 mM | 67 (67) |
| 3 | 13 mM | 17 (21) |

Table 4 lists effect of water ratio on THCQ yield. All entries in Table 4 are carried out in 0.1 M NBu$_4$BF$_4$ electrolyte dissolved in MeCN with a Pt anode and a graphite cathode. During the reaction, a constant current of about 7.9 mA is applied with alternating terminal polarity every 60 seconds for about 1 hour at 23° C. In Entry 1, electrolyte (0.100 M NBu$_4$BF$_4$ in MeCN, 6.6 mM) is used followed by water. The electrolyte and water ratio is 100 to 1. Entry 1 achieves no conversion from THC to THCQ. In Entry 2, electrolyte (0.100 M NBu$_4$BF$_4$ in MeCN, 6.6 mM) is used followed by water. The electrolyte and water ratio is 80 to 1. Entry 2 achieves about 5% yield of THCQ from THC. In Entry 3, electrolyte (0.100 M NBu$_4$BF$_4$ in MeCN, 6.6 mM) is used followed by water. The electrolyte and water ratio is 8 to 1. Entry 3 achieves about 67% yield of THCQ from THC. In Entry 4, electrolyte (0.100 M NBu$_4$BF$_4$ in MeCN, 6.6 mM) is used followed by water. The electrolyte and water ratio is 1 to 1. Entry 4 achieves about 11% yield of THCQ from THC.

TABLE 4

Effect of water ratio on % yield.

| Entry | Electrolyte:Water | % Yield (brsm) |
|---|---|---|
| 1 | 100:1 | 0 (0) |
| 2 | 80:1 | 5 (17) |
| 3 | 8:1 | 67 (67) |
| 4 | 1:1 | 11 (15) |

Table 5 lists effect of current on THCQ yield. All entries in Table 5 are carried out in 0.1 M $NBu_4BF_4$ electrolyte dissolved in MeCN with a Pt anode and a graphite cathode. During the reaction, a constant current is applied with alternating terminal polarity every 60 seconds for about 1 hour at 23° C. In Entry 1, a constant current of about 3.9 mA is applied. Entry 1 achieves about 34% yield of THCQ. In Entry 2, a constant current of about 7.9 mA is applied. Entry 1 achieves about 67% yield of THCQ. In Entry 3, a constant current of about 16 mA is applied. Entry 1 achieves 0% yield of THCQ.

TABLE 5

Effect of current on % yield.

| Entry | Current (mA) | % Yield (brsm) |
|---|---|---|
| 1 | 3.90 | 34 (56) |
| 2 | 7.90 | 67 (67) |
| 3 | 16.0 | 0 (0) |

Table 6 lists effect of additives on THCQ yield. All entries in Table 5 are carried out in 0.1 M $NBu_4BF_4$ electrolyte dissolved in MeCN with a Pt anode and a graphite cathode. During the reaction, a constant current of about 7.9 mA is applied for about 1 hour at 23° C. In Entry 1, 1 equiv of $H_2O_2$ is added to the electrolyte. Entry 1 achieves about 45% yield of THCQ. In Entry 2, 1 equiv of tBuOOH is added to the electrolyte. Entry 2 achieves 0% yield of THCQ. In Entry 3, 1 equiv of $NBu_4OH$ is added to the electrolyte. Entry 3 achieves 0% yield of THCQ. In Entry 4, 1 equiv of $(tBuO)_2OPONBu_4$ is added to the electrolyte. Entry 4 achieves about 12% yield of THCQ. In Entry 6, 1 equiv of $Cl_4NHPI$ is added to the electrolyte. Entry 6 achieves about 32% yield of THCQ.

TABLE 6

Effect of additives on % yield.

| Entry | Additive (1 equiv) | % Yield (brsm) |
|---|---|---|
| 1 | $H_2O_2$ | 45 (73) |
| 2 | tBuOOH | 0 (0) |
| 3 | $NBu_4OH$ | 0 (0) |
| 4 | $(tBuO)_2OPONBu_4$ | 12 (12) |
| 6 | $Cl_4NHPI$ | 32 (32) |

Chemical Oxidation Methods of THC to THCQ

Figure 9:
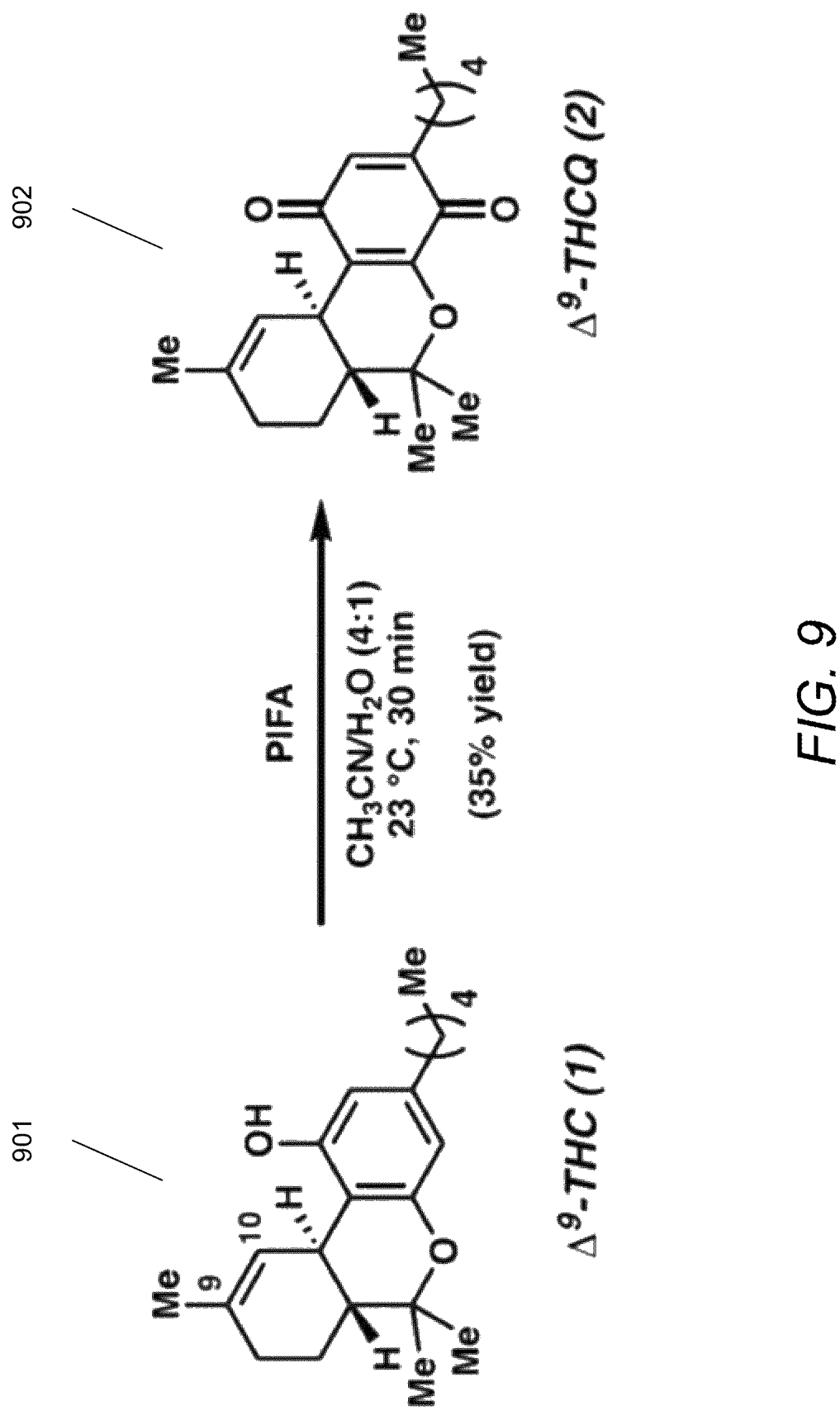
FIG. 9 illustrates the chemical oxidation of $\Delta^9$-THC to $\Delta^9$-THCQ in accordance with an embodiment.

Several embodiments implement a chemical method to oxidize THC. Some embodiments evaluate the photophysical and electrochemical properties of oxidized product $\Delta^9$-THCQ. The chemical oxidation of the alkene isomer $\Delta^8$-THC to the corresponding $\Delta^8$-THCQ had been previously reported, (See, e.g., Kogan, N. M., et al.. *J. Med. Chem.* 2004, 47, 3800-3806; Kogan, N. M., et al., *Mol. Pharmacol.* 2006, 70, 51-59; Mechoulam, R., U.S. Pat. No. 8,497,299 B2; Mechoulam, R., International Patent No. WO 2005,067917 A1; and Osman, A. G., *Eur. J. Med. Chem.* 2018, 143, 983-996, the disclosures of which are incorporated herein by reference.) In this report, the authors were able to use a hypervalent reagent, bis(trifluoroacetoxy)iodobenzene (PIFA), to oxidize $\Delta^8$-THC to the corresponding p-quinone. The $\Delta^8$-THC isomer was oxidized for applications in cancer therapeutics. In comparison, $\Delta^9$-THC is more abundant in marijuana than $\Delta^8$-THC. Many embodiments implement PIFA in oxidizing $\Delta^9$-THC to the corresponding quinone. An example of chemical oxidation process is illustrated in FIG. 9 in accordance with an embodiment of the invention. THC (901) can be oxidized to THCQ (902) in PIFA dissolved in $CH_3CN$ at $_{23}$° C. The reaction can take about 30 minutes. The corresponding $\Delta^9$-THCQ can be formed in about 34% yield along with a number of additional oxidations products.

Figure 10:
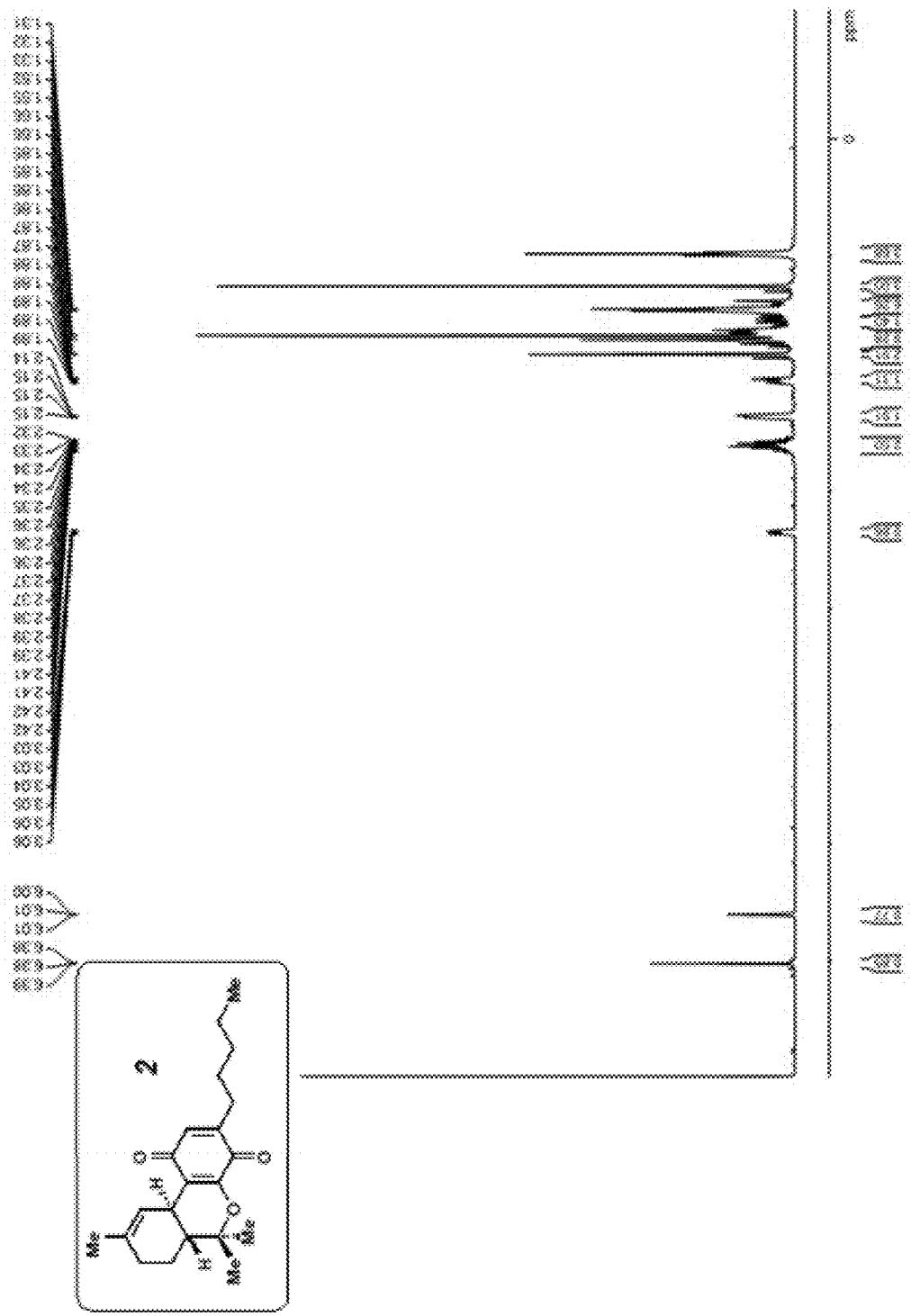
FIG. 10 illustrates a $^1$H-NMR spectrum of $\Delta^9$-THCQ in accordance with an embodiment.
Figure 11:
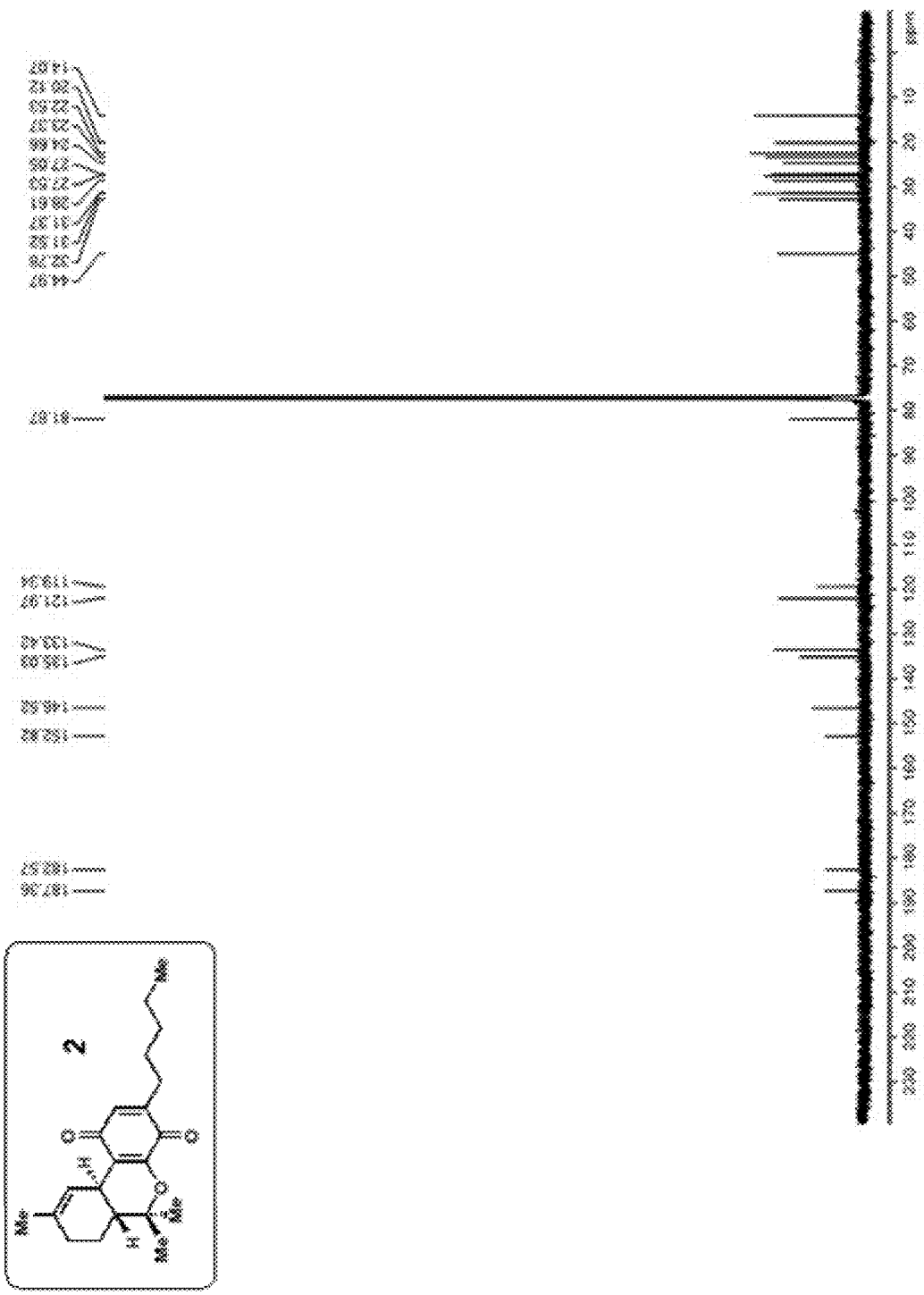
FIG. 11 illustrates a $^{13}$C-NMR spectrum of $\Delta^9$-THCQ in accordance with an embodiment.
Figure 12A:
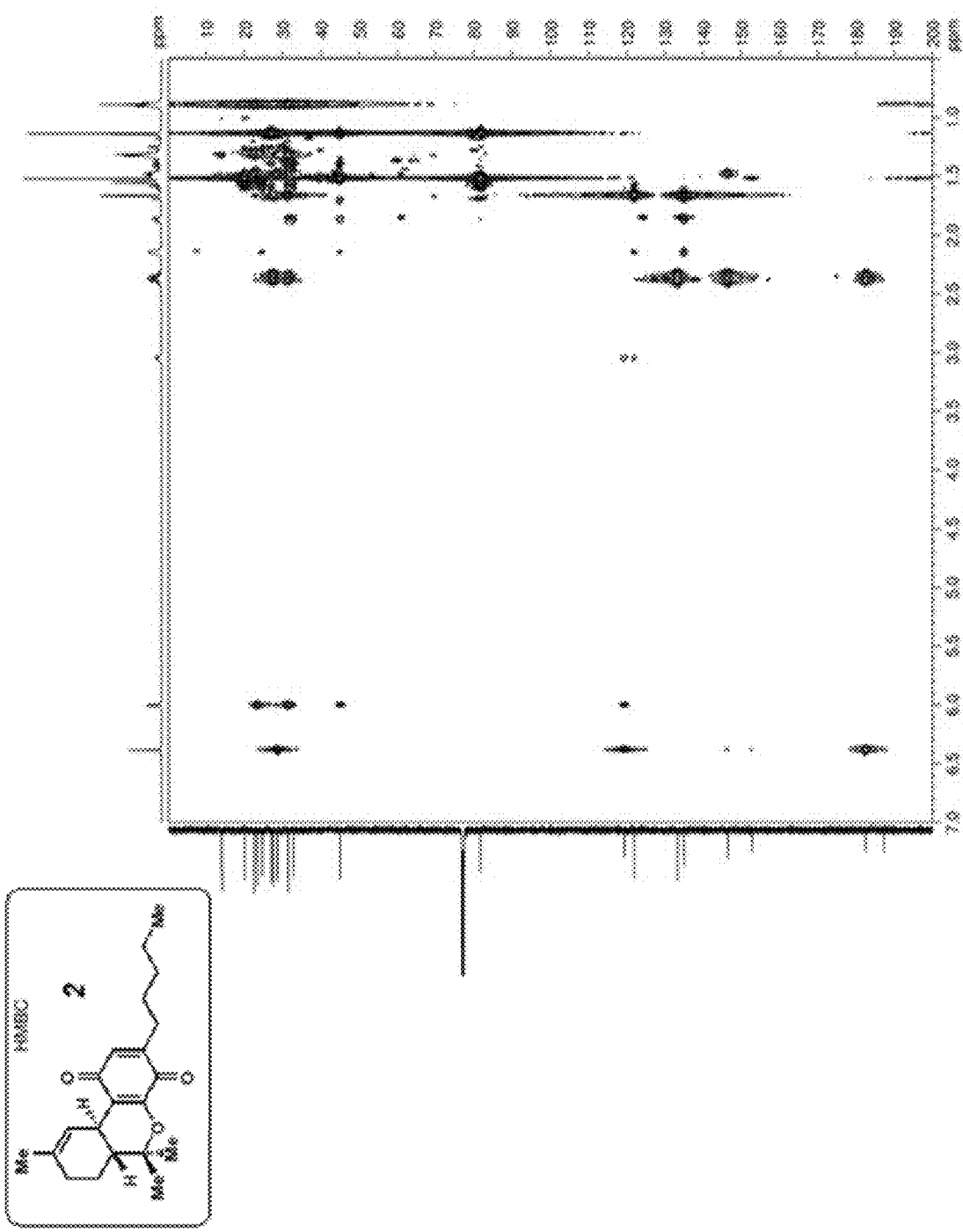
FIGS. 12A-12E illustrate 2D-NMR spectra of $\Delta^9$-THCQ in accordance with an embodiment.
Figure 12B:
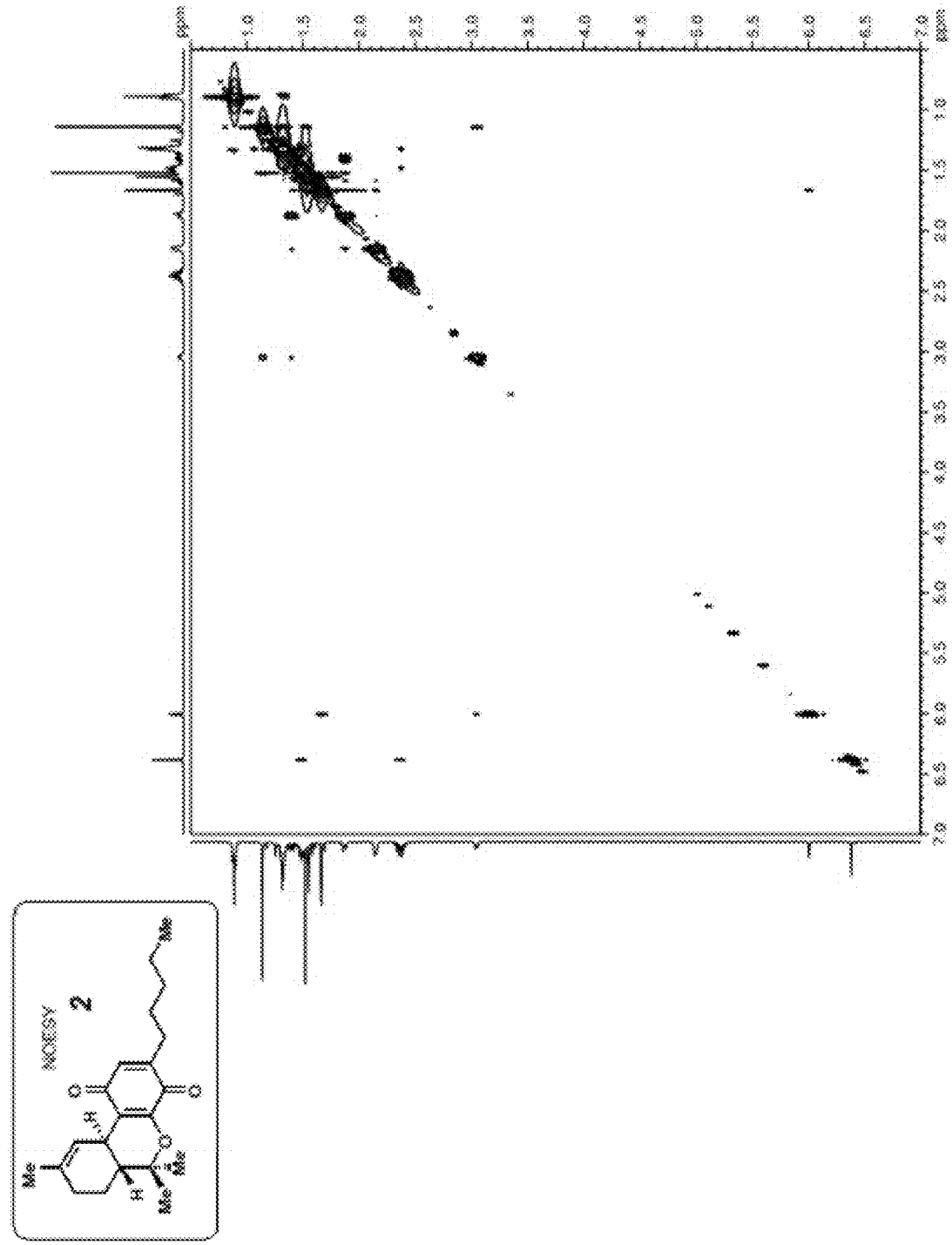
Figure 12C:
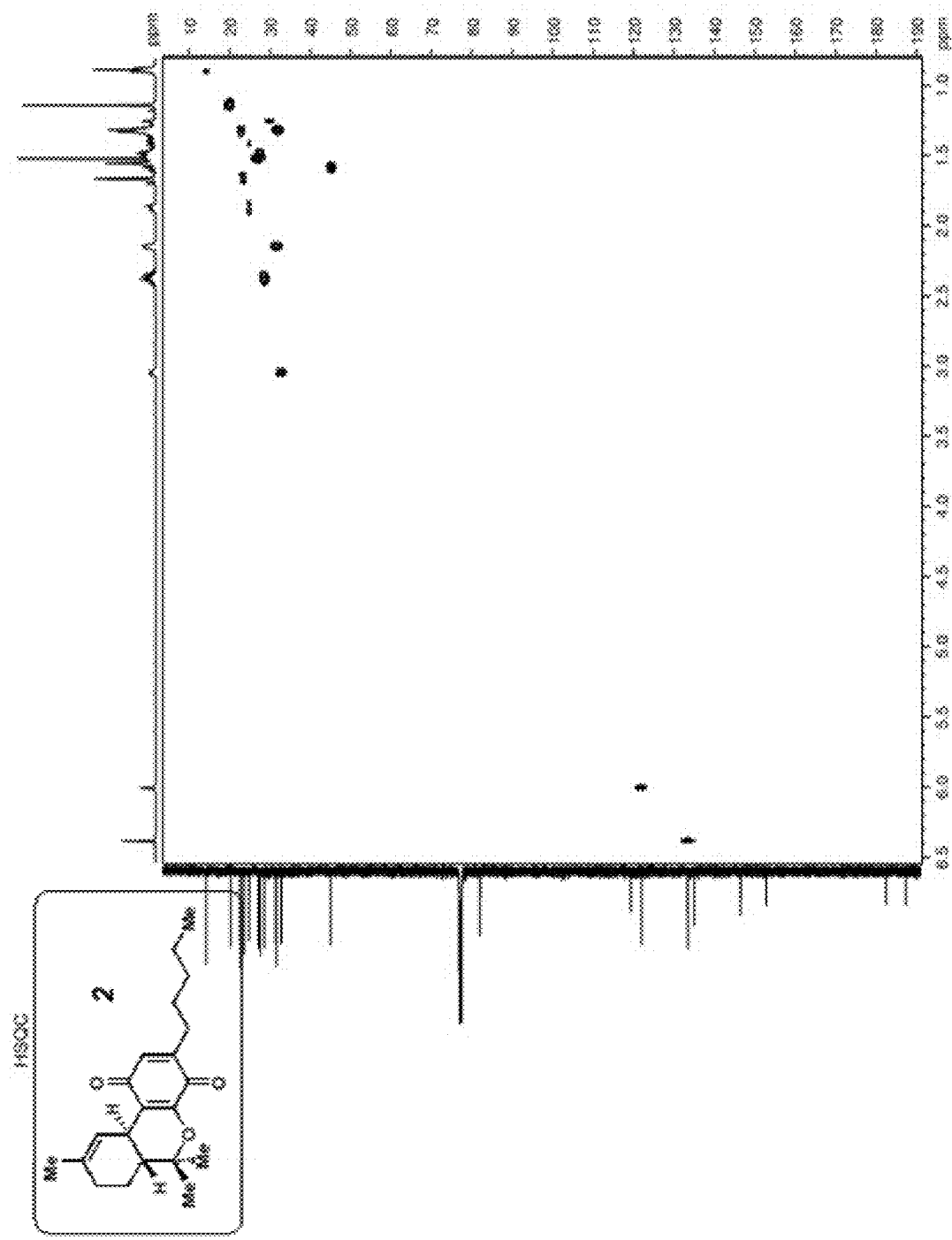
Figure 12D:
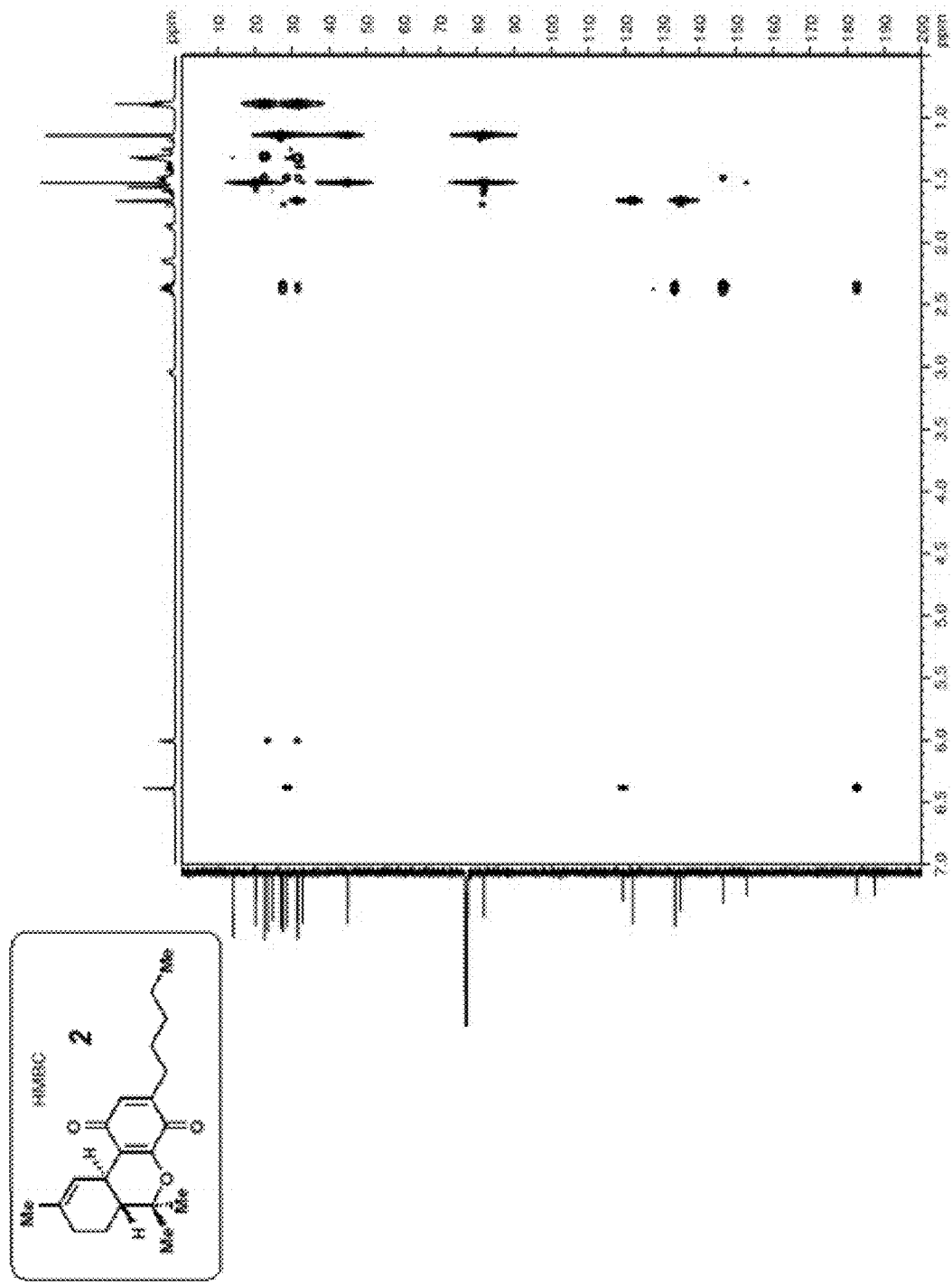
Figure 12E:
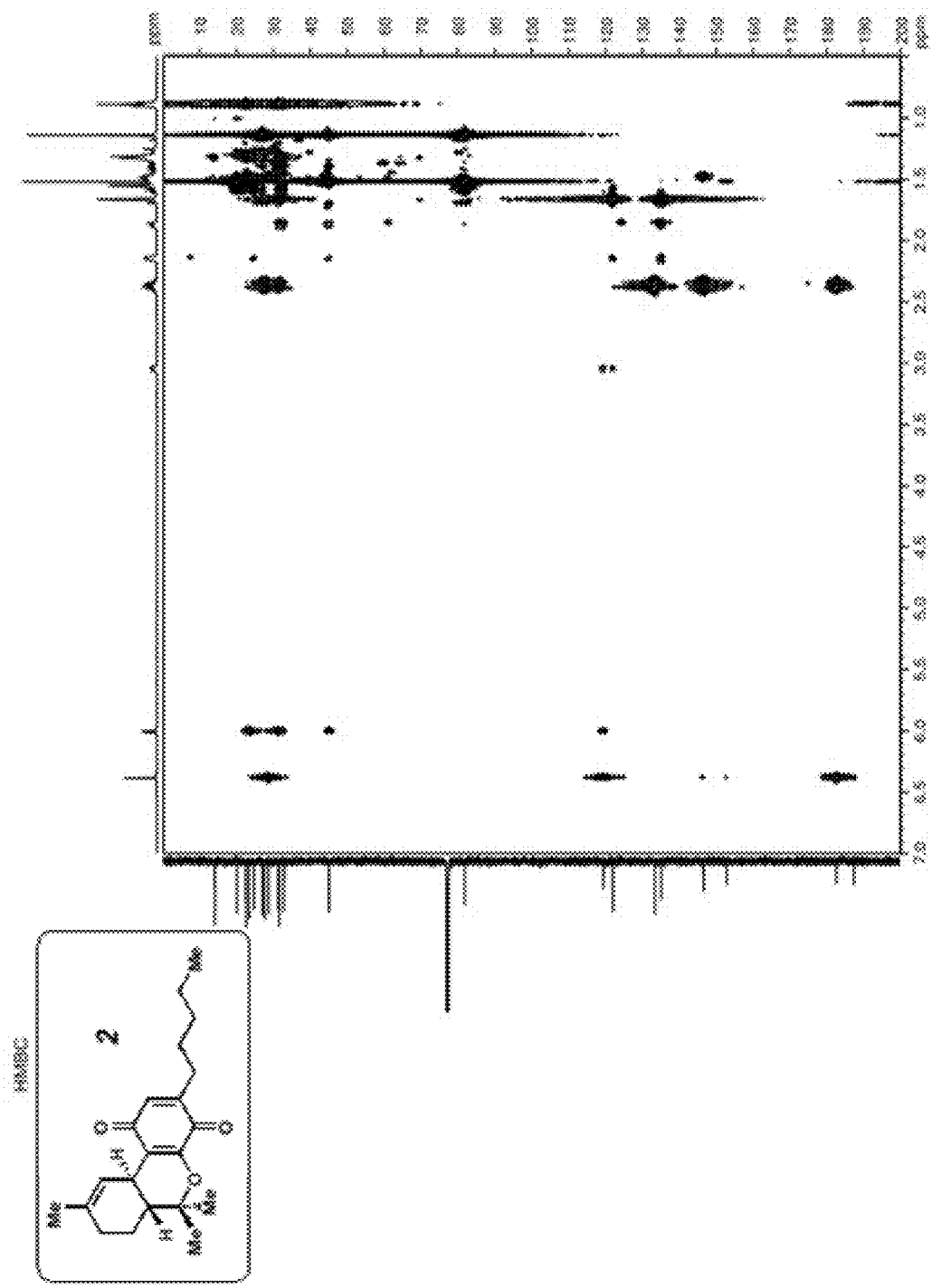

Many embodiments implements product isolation and characterization of THCQ. Several embodiments implement NMR spectroscopy to characterize the identity and purity of THCQ. FIGS. 10 and 11 illustrate NMR spectra of THCQ in accordance with an embodiment. The structure of $\Delta^9$-THCQ can be assigned in $^1$H-NMR spectrum shown in FIG. 10. The structure of $\Delta^9$-THCQ can be assigned in $^{13}$C-NMR spectrum shown in FIG. 11.

In some embodiments, 2D NMR spectroscopy can be used to show the desired p-quinone as opposed to the o-quinone and supported an alkene in the 9-position as opposed to the more thermodynamically favored 8-position. FIGS. 12A-12E illustrate 2D NMR spectra of THCQ in accordance with an embodiment.

Figure 13:
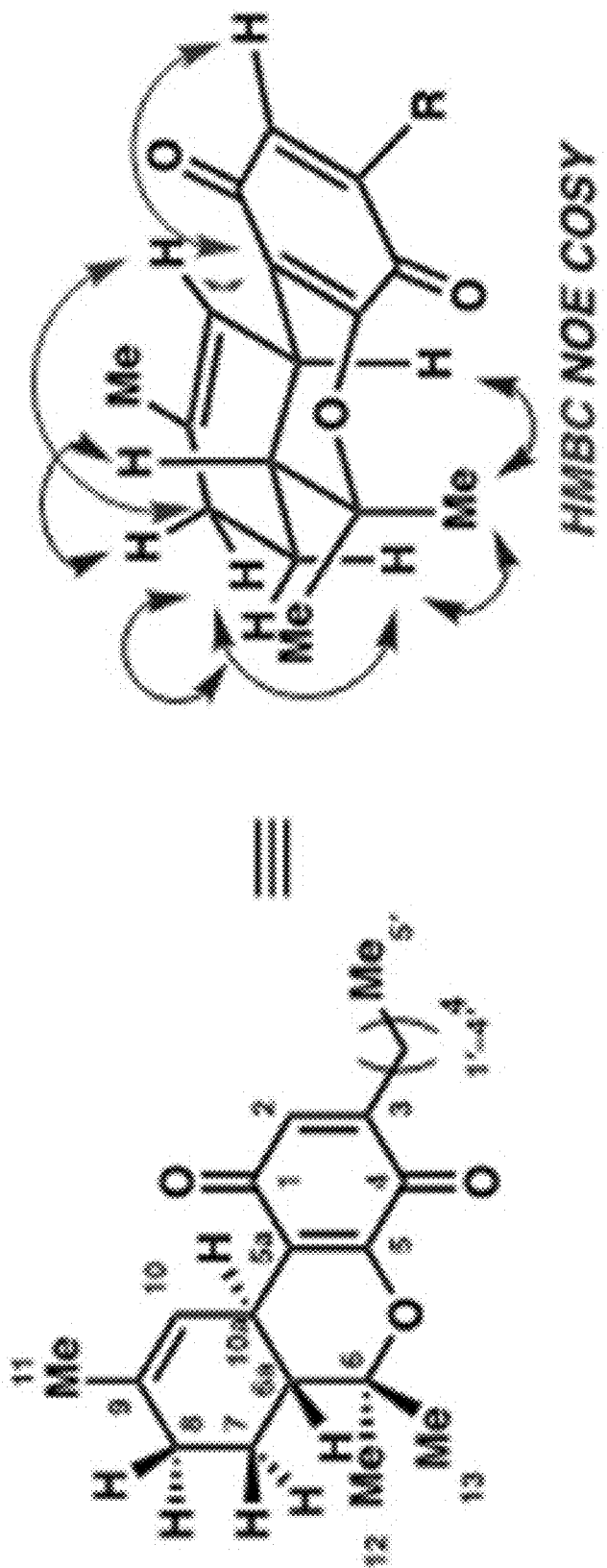
FIG. 13 illustrates the $\Delta^9$-THCQ correlation in accordance with an embodiment.

In many embodiments, the structure of $\Delta^9$-THCQ can be numbered according to modern conventions and can be assigned using a variety of NMR techniques. An example of THCQ structural assignment is illustrate FIG. 13 in accordance with an embodiment of the invention. First, the alkene position is assigned according to COSY interaction between H10*a* and H10 as well as an HMBC correlation between H10 to C5*a*, C8, C9, and C11. Additionally, an HMBC between H10*a* to C6*a* , C10, and C5*a* support the assignment of the alkene.

Figure 14:
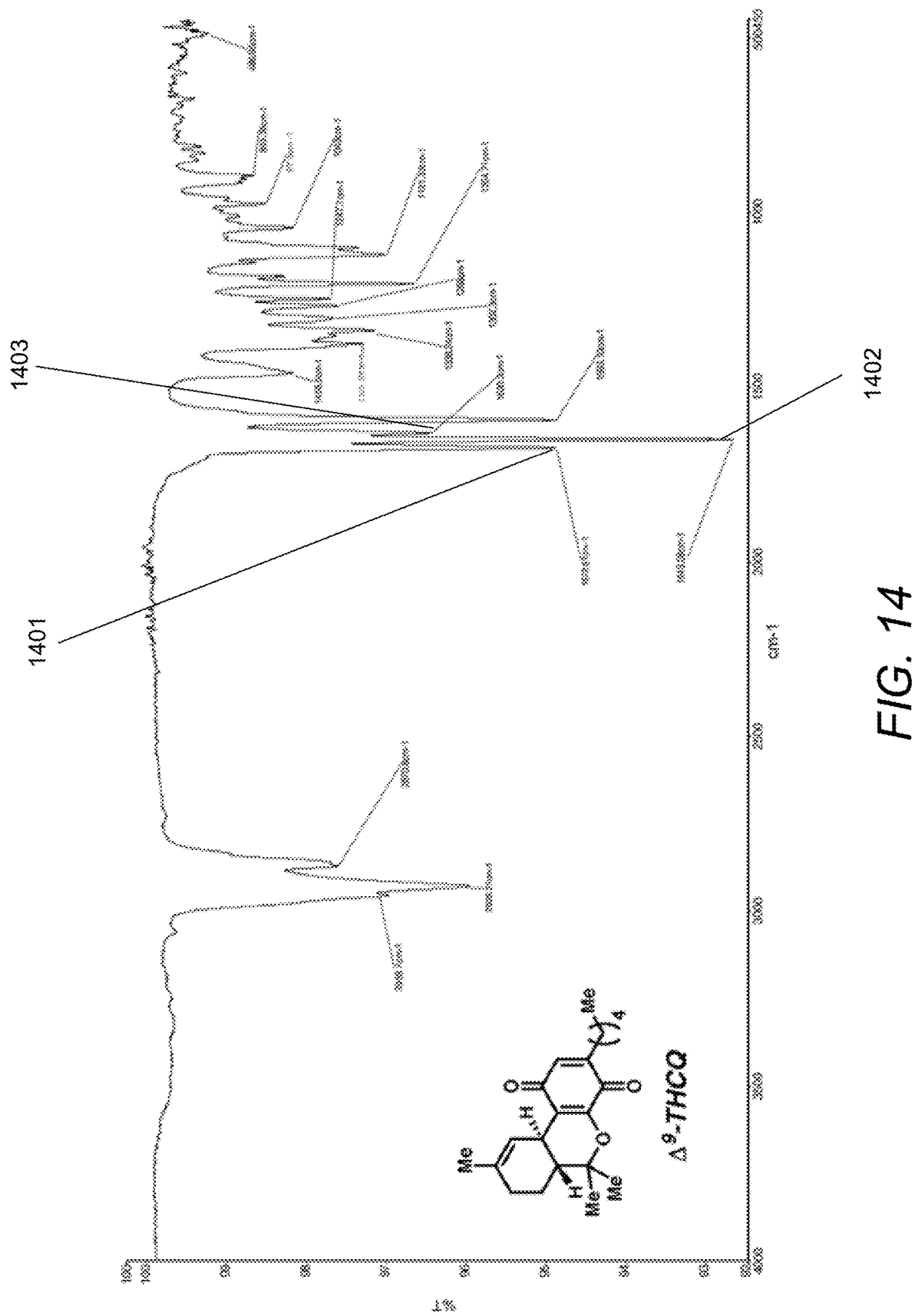
FIG. 14 illustrates a infrared spectrum of $\Delta^9$-THCQ in accordance with an embodiment.

Several embodiments implement infrared (IR) spectroscopy to characterize the THCQ product. FIG. 14 illustrates an IR spectrum of THCQ in accordance with an embodiment of the invention. In FIG. 14, the additional carbonyl stretches at 1673 $cm^{-1}$ (1401), 1649 $cm^{-1}$ (1402), and 1630 $cm^{-1}$ (1403) are indicative of the THCQ quinone.

Figure 15:
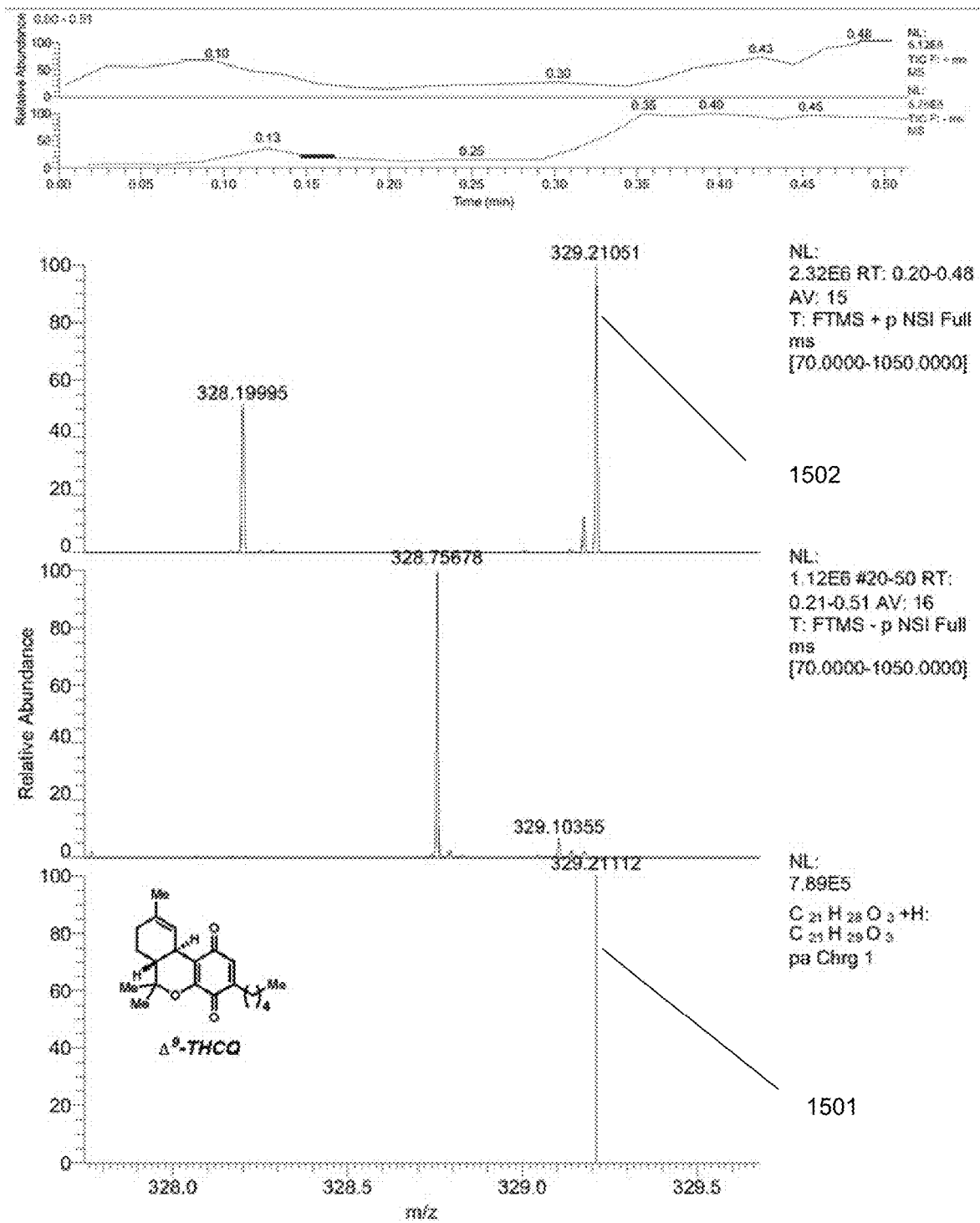
FIG. 15 illustrates a mass spectrometry spectrum of $\Delta^9$-THCQ in accordance with an embodiment.

Some embodiments implement mass spectrometry to characterize the THCQ product. FIG. 15 illustrates a high resolution mass spectrum of THCQ in accordance with an embodiment of the invention. In FIG. 15, the [M+H] molecular ion $C_{21}H_{29}O_3^+$, 329.2112 (1501); 329.2105 (1502) are indicative of the THCQ quinone.

Photophysical Properties of THC and THCQ

In many embodiments, THCQ may show strong visible light absorbance and THC may not show visible light absorbance. In some embodiments, THCQ shows optical absorbance in the UV spectrum and visible spectrum. Several embodiments demonstrate that THC can have absorbances in the UV region with major peaks at around 208 nm, 232 nm, and 282 nm. Several embodiments demonstrate that THCQ can exihibit strong absorbance peaks in the UV region at wavelength around 204 nm and 266 nm, and a strong peak in the visible light region at wavelength around 402 nm.

Figure 16:
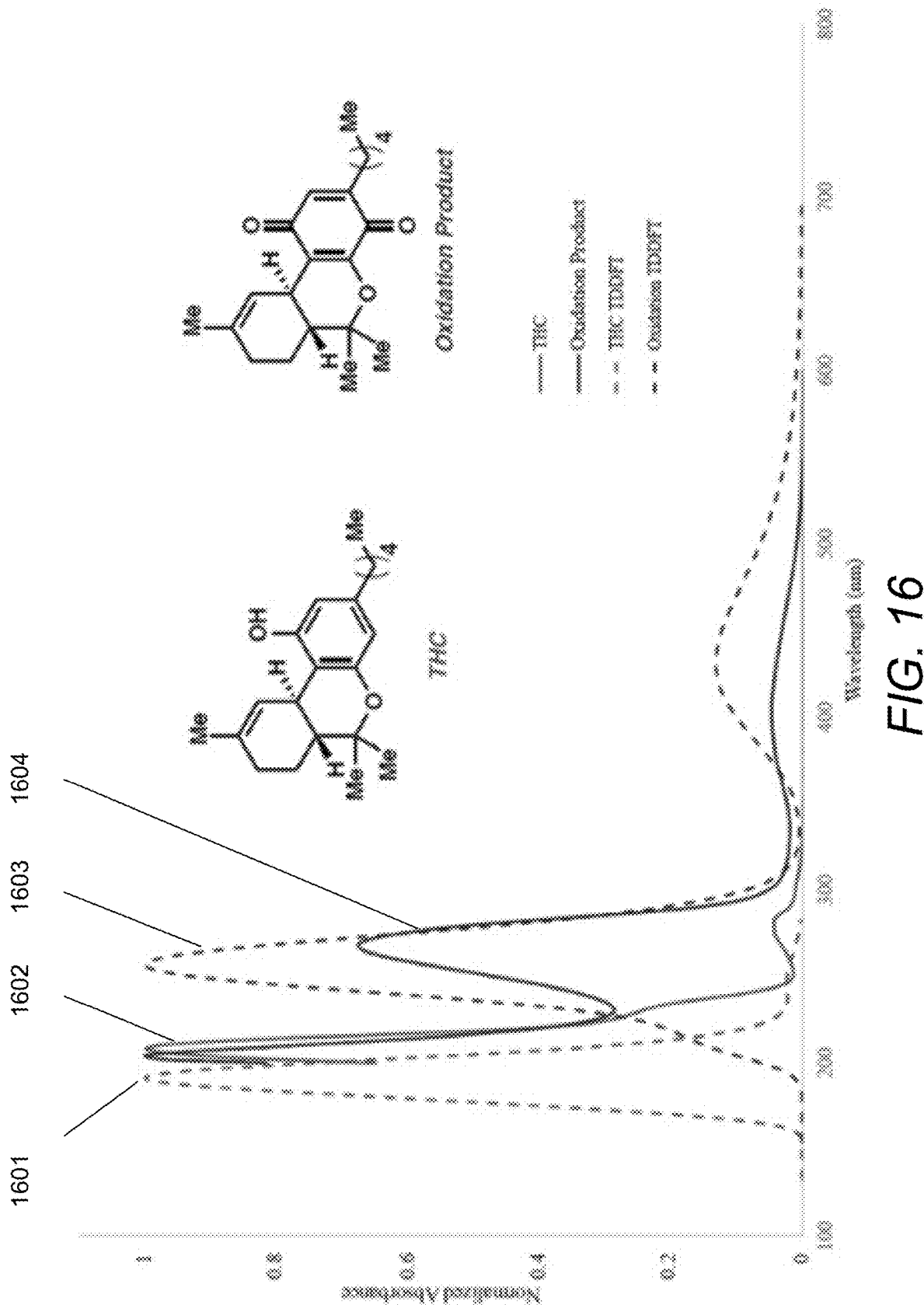
FIG. 16 illustrates UV absorption spectra of $\Delta^9$-THC and $\Delta^9$-THCQ in accordance with an embodiment.

Many embodiments compare and contrast photophysical properties changes of $\Delta^9$-THCQ with $\Delta^9$-THC. These differences can allow for THC breathalyzer systems according to many embodiments. Some embodiments investigate the photophysical properties using UV/Vis spectroscopy. An example of THC and THCQ UV/Vis spectrum is illustrated in FIG. 16 in accordance with an embodiments. The UV/Vis spectrum of $\Delta^9$-THC (1602) show absorbances in the UV region with major peaks at 208 nm, 232 nm, and 282 nm. The oxidized $\Delta^9$-THCQ (1604) show strong absorbance peaks in the UV region at 204 nm and 266 nm, as well as a diagnostic peak in the visible spectrum at 402 nm. The strong correlation with the TDDFT calculations for both $\Delta^9$-THC (1601) and $\Delta^9$-THCQ (1603) provides further insight to investigate the differences between these two spectra.

Figure 17:
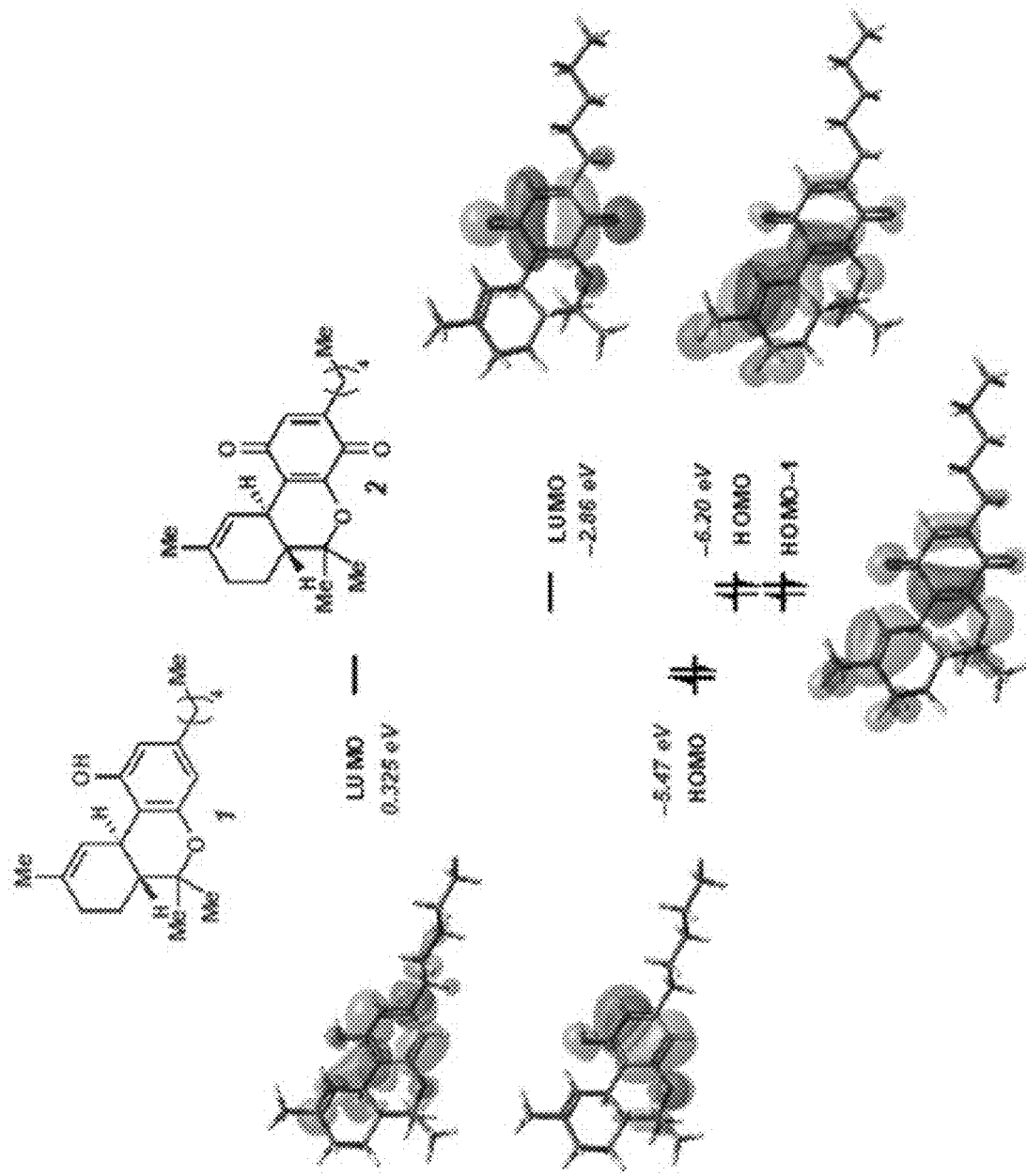
FIG. 17 illustrates the HOMO and LUMO energy levels and orbital distributions of $\Delta^9$-THC and $\Delta^9$-THCQ in accordance with an embodiment.

UV/Vis spectrum data of the orbital contributions to the key electronic transitions as well as the orbital distributions and energies show differences in the spectra for $\Delta^9$-THC and $\Delta^9$-THCQ in accordance with several embodiments. An example of DFT calculated HOMO and LUMO energy levels and orbital distributions for THC and THCQ is illustrated in FIG. 17 in accordance with an embodiment. The lowest energy transition for $\Delta^9$-THC has an experimental peak at 282 nm and can be found to be primarily comprised of the HOMO-LUMO transition with orbital densities of both located on the electron rich aromatic system. The red shifted visible absorbance for $\Delta^9$-THCQ can be found to be comprised of a combination of the HOMO-LUMO and HOMO-1-LUMO transition. In this case, the HOMO and HOMO-1 are distributed over the electron rich alkene while the LUMO is localized on the electron poor quinone. This $\pi$-$\pi$* transition can be a donor-acceptor interaction. The electronegative carbonyl groups may lead to a net lowering of the LUMO energy, a narrowing of the HOMO-LUMO transition energy, and ultimately a red-shift into the visible spectrum for $\Delta^9$-THCQ relative to $\Delta^9$-THC.

Electrochemical Properties of THC and THCQ

Figure 18A:
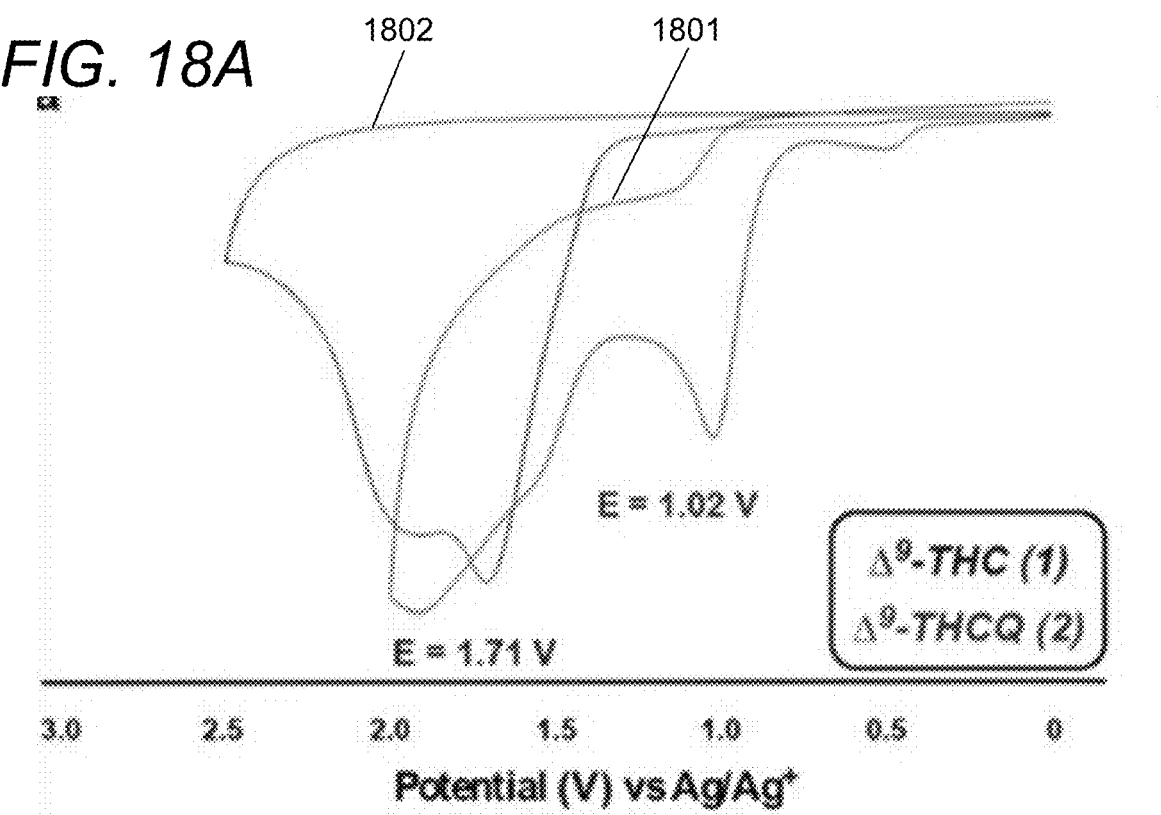
FIG. 18A illustrates the electrochemical oxidation potential of $\Delta^9$-THC and $\Delta^9$-THCQ in accordance with an embodiment.
Figure 18B:
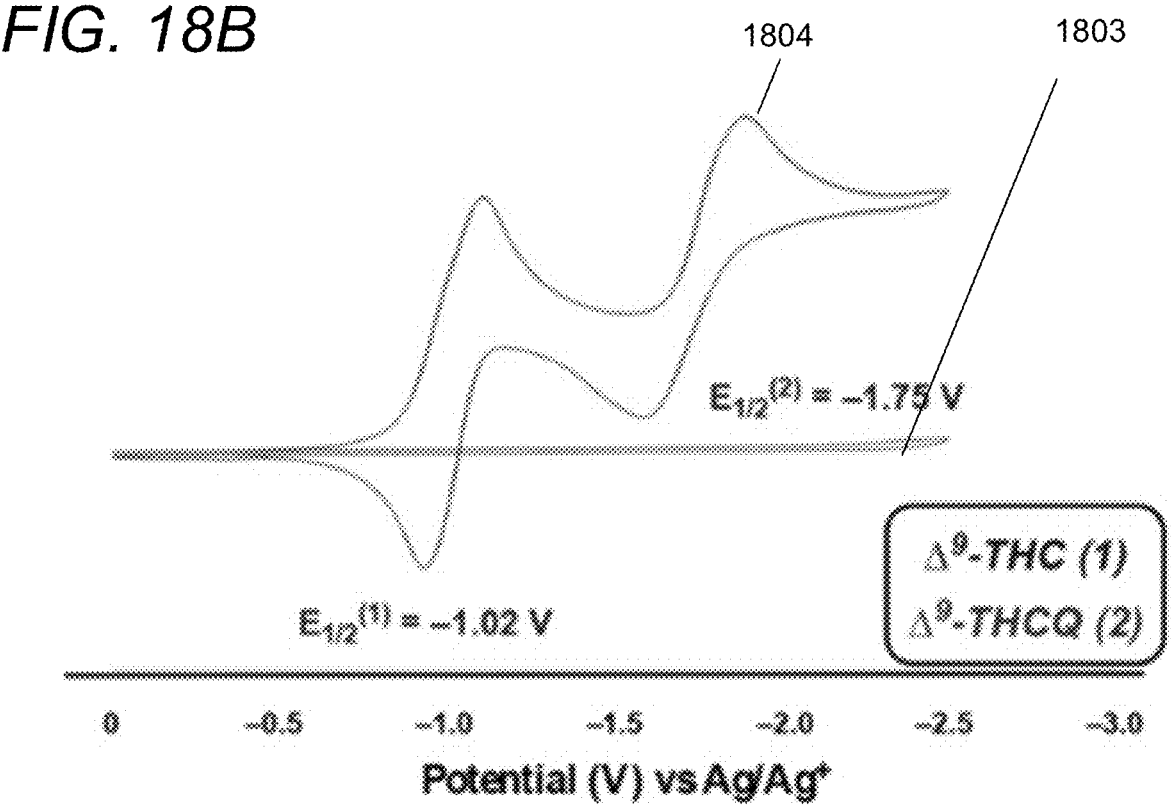
FIG. 18B illustrates the electrochemical reduction potential of $\Delta^9$-THC and $\Delta^9$-THCQ in accordance with an embodiment.

Many embodiments implement cyclic voltammetry to assess differences in redox potentials between $\Delta^9$-THC and $\Delta^9$-THCQ. An example of oxidation potential and reduction potential of THC and THCQ is illustrated FIGS. 18A-18B in accordance with an embodiment. In FIG. 18A, the oxidation potential for $\Delta^9$-THC (1801) shows an irreversible oxidation event at a peak potential of 1.02 V in line with reported values for $\Delta^9$-THC. The measured oxidation potentials for $\Delta^9$-THCQ (1802) shows an irreversible oxidation event at around 1.71 V, along with a broad peak at around 1.92 V. This shift in oxidation potential (1802) can be understood based on the DFT calculations in FIG. 17, where removal of an electron from the HOMO of $\Delta^9$-THC would be more favorable than the lower lying HOMO for $\Delta^9$-THCQ. The reduction potentials for $\Delta^9$-THC (1803) and $\Delta^9$-THCQ (1804) are shown in FIG. 18B. For $\Delta^9$-THC (1803), a negative scan from 0.0 V to $-2.5$ V shows no measurable reduction events indicative of an inaccessible LUMO energy. Reduction of $\Delta^9$-THCQ (1804) shows two reversible reduction events at $E_{1/2}^{(1)}$ at around $-1.02$ V and $E_{1/2}^{(2)}$ at around $-1.75$ V. The reduction events for $\Delta^9$-THCQ are thought to arise from a single electron reduction to the semiquinone and a second single electron reduction to arrive at the hydroquinone.

Exemplary Embodiments

The following embodiments provide specific combinations of materials and processes for the oxidation of $\Delta^9$-THC to $\Delta^9$-THCQ. It will be understood that the specific embodiments are provided for exemplary purposes and are not limiting to the overall scope of the disclosure, which must be considered in light of the entire specification, figures and claims.

Example 1: Electrochemical Oxidation Methods

A 5 mL ElectraSyn™ 2.0 vial equipped with a stir bar is flame dried under reduced pressure and is cooled to 23° C. under nitrogen. Next, the $\Delta^9$-THC solution (0.280 mL of 25 mg/mL solution in ethanol; 7.00 mg, 22.3 µmol, 1.00 equiv) is added to this vial which is then concentrated under reduced pressure to afford a clear oil. Electrolyte (3.00 mL, NBu$_4$BF$_4$ 0.100 M in MeCN, 6.60 mM) is then added to the vial followed by water (0.400 mL), as described in FIGS. 5a and 5b. The solution is stirred open to air from 60 seconds to ensure full dissolution of the substrate. Next, the vial is equipped with a platinum anode and a graphite cathode. This vial is then connected to the ElectraSyn™ 2.0 instrument is set to run for 60 minutes under a constant current of 7.9 mA and at a stir rate of 400 rpm. The polarity is set to alternate every 60 seconds to reduce build up at each electrode over the course of the reaction. Once the reaction is complete, the reaction is diluted with saturated sodium bicarbonate (1.00 mL) and is extracted with diethyl ether (3×2.00 mL). The organic layers are cooled and are subsequently washed with water (3×2.00 mL) and brine (2.00 mL). Finally, the organic solution is dried over sodium sulfate (0.500 g) and is filtered over cotton. This crude reaction solution is concentrated under reduced pressure to give an orange oil. This orange oil is dissolved in CH$_2$Cl$_2$ (0.300 mL) and is loaded onto a prep plate which is then developed with 100% benzene.

Cyclic voltammetry spectra are measured using a C-H Instruments CHI620E potentiostat. The analyte (5.00 mM) is dissolved in dry degassed 0.1 M NBu$_4$BF$_4$ in MeCN. Spectra are collected at a sweep rate of 100 mV/s at 23° C. Ferrocene (99% purity) is added to each sample after each scan for reference. All spectra are collected using a glassy carbon working electrode, a platinum counter electrode, and a Ag/Ag+reference electrode. The reference electrode is prepared with a 10 mM solution of AgNO$_3$ (99.9% purity) in MeCN. The platinum wire is heated with a Bunsen burner till it glowed prior to each measurement. The glassy working electrode is polished to a mirror using 0.05 micron MicroPolish™ powder prior to each measurement.

Example 2: Chemical Oxidation Methods

A 5 mL round bottom flask equipped with a stir bar was flame dried under reduced pressure and is cooled to 23° C. under nitrogen. A THC solution (1.00 mL of 25 mg/mL solution in ethanol; 25.0 mg, 79.5 µmol, 1.00 equiv) is added to this flask and is concentrated under reduced pressure to a clear oil. Next, MeCN (2.50 mL) and water (0.500 mL) are sequentially added to this vial to dissolved the THC. A second 5 mL round bottom flask is flame dried under reduces pressure and was cooled to 23° C. under nitrogen. To this flask is added PIFA (103 mg, 238 µmol, 3.00 equiv) which is subsequently dissolved in MeCN (2.50 mL). The PIFA solution is then added to the THC solution dropwise over 2 minutes resulting in a yellow solution. This reaction is stirred for an additional 30 min at which point it is quenched with saturated NaHCO$_3$ (1.00 mL). The reaction is diluted with water (2.00 mL) and is extracted with EtOAc (3×1.00 mL). The organic layers are pooled and washed with water (3×1.00 mL) and brine (1.00 mL) and is dried over sodium sulfate. The solution is filtered over cotton and was then concentrated under reduced pressure to give a yellow oil. This crude material is dissolved in $CH_2Cl_2$ (0.400 mL) is loaded onto a prep plate which is subsequently developed with 100% benzene to give the desired product (9.00 mg, 35% yield) as an orange oil.

Doctrine of Equivalents

As can be inferred from the above discussion, the above-mentioned concepts can be implemented in a variety of arrangements in accordance with embodiments of the invention. Accordingly, although the present invention has been described in certain specific aspects, many additional modifications and variations would be apparent to those skilled in the art. It is therefore to be understood that the present invention may be practiced otherwise than specifically described. Thus, embodiments of the present invention should be considered in all respects as illustrative and not restrictive.

What is claimed is:

1. A method of detecting tetrahydrocannabinol ($\Delta^9$-THC) comprising:
    obtaining a sample from a source;
    disposing the sample in a solution;
    oxidizing the sample either chemically or electrochemically;
    analyzing properties of the oxidized sample selected from the group consisting of photochemical properties, electronic properties, and spectroscopic properties;
    identifying tetrahydrocannabinol p-quinone ($\Delta^9$-THCQ) specific features in properties selected from the group consisting of photochemical properties, electronic properties, and spectroscopic properties; and
    determining if $\Delta^9$-THCQ is present in the oxidized sample.

2. The method of claim 1, wherein the sample is either in liquid phase or in gas phase.

3. The method of claim 1, wherein the sample is a biological sample extracted from an individual and the biological sample is biofluid, tear, saliva, mucus, urine, sweat, blood, or plasma.

4. The method of claim 1, wherein the sample is in gas phase and the sample is breath.

5. The method of claim 1, wherein the solution comprises an electrolyte dissolved in a solvent, wherein the solvent is selected from the group consisting of an aqueous solvent, an organic solvent, and a mixture of an aqueous solvent and an organic solvent.

6. The method of claim 1, wherein the solution comprises $NBu_4BF_4$, or $LiClO_4$ dissolved in a solvent, wherein the solvent is selected from the group consisting of an aqueous solvent, an organic solvent, and a mixture of an aqueous solvent and an organic solvent.

7. The method of claim 1, wherein the solution comprises $NBu_4BF_4$ and a redox mediator N-hydroxytetrachlorophthalimide ($Cl_4NHPI$) and the sample is oxidized electrochemically.

8. The method of claim 7, wherein the oxidizing process is a controlled electrochemical process.

9. The method of claim 8, wherein the controlled oxidation of $\Delta^9$-THC to $\Delta^9$-THCQ has an efficiency of at least 67%.

10. The method of claim 1, wherein the solution comprises bis (trifluoroacetoxy) iodobenzene (PIFA) and the sample is oxidized chemically.

11. The method of claim 1, wherein $\Delta^9$-THCQ specific features in photochemical properties comprise optical absorbance in UV spectrum and visible light spectrum.

12. The method of claim 11, wherein optical absorbance of $\Delta^9$-THCQ in UV spectrum at wavelength between 200 nm and 300 nm, and in visible light spectrum at wavelength between 350 nm and 500 nm with a peak at around 402 nm.

13. The method of claim 1, wherein $\Delta^9$-THCQ specific features in electrochemical properties comprise at least one oxidation potential and at least one reduction potential.

14. The method of claim 8, wherein the controlled oxidation of $\Delta^9$-THC to $\Delta^9$-THCQ has an efficiency of at least 20%.

15. The method of claim 1, wherein the electrochemical oxidation comprises at least one cathode and at least one anode.

16. The method of claim 15, wherein the cathode is graphite, glassy carbon, or platinum.

17. The method of claim 15, wherein the anode is graphite or platinum.

18. The method of claim 15, wherein the cathode is graphite and the anode is platinum.

19. The method of claim 15, wherein the cathode is platinum and the anode is platinum.

20. The method of claim 15, wherein the cathode is glassy carbon and the anode is platinum.

* * * * *